United States Patent
Yamamoto et al.

(10) Patent No.: US 9,095,637 B2
(45) Date of Patent: Aug. 4, 2015

(54) ION GENERATOR AND AIR CLEANER

(75) Inventors: Akira Yamamoto, Osaka (JP); Motoyuki Suzuki, Osaka (JP); Naoki Wada, Osaka (JP)

(73) Assignees: SHARP KABUSHIKI KAISHA, Osaka (JP); JAPAN CASH MACHINE CO., LTD., Osaka (JP)

( * ) Notice: Subject to any disclaimer, the term of this patent is extended or adjusted under 35 U.S.C. 154(b) by 196 days.

(21) Appl. No.: 13/704,189

(22) PCT Filed: Jun. 13, 2011

(86) PCT No.: PCT/JP2011/063447
§ 371 (c)(1),
(2), (4) Date: Dec. 13, 2012

(87) PCT Pub. No.: WO2011/158770
PCT Pub. Date: Dec. 22, 2011

(65) Prior Publication Data
US 2013/0095000 A1    Apr. 18, 2013

(30) Foreign Application Priority Data

Jun. 15, 2010  (JP) .................. 2010-135959
Oct. 26, 2010  (JP) .................. 2010-239925

(51) Int. Cl.
| | |
|---|---|
| A61L 9/00 | (2006.01) |
| B01D 19/00 | (2006.01) |
| B01D 39/00 | (2006.01) |
| A61L 9/22 | (2006.01) |
| F24F 3/16 | (2006.01) |
| H01T 23/00 | (2006.01) |
| H01J 27/02 | (2006.01) |

(52) U.S. Cl.
CPC . *A61L 9/22* (2013.01); *F24F 3/166* (2013.01); *H01J 27/02* (2013.01); *H01T 23/00* (2013.01); *A61L 2209/212* (2013.01); *F24F 2003/1682* (2013.01)

(58) Field of Classification Search
CPC ............. A61L 9/00; A61L 9/03; A61L 9/032; A61L 9/16
USPC .................. 422/5, 22, 121, 124, 186.04, 306, 422/906–907; 55/472, 486; 96/225, 243; 95/57
See application file for complete search history.

(56) References Cited

U.S. PATENT DOCUMENTS 7,040,101 B2 * 5/2006 Takeda et al. ................... 62/78

FOREIGN PATENT DOCUMENTS

| | | |
|---|---|---|
| JP | 9-245934 A | 9/1997 |
| JP | 2002-95998 A | 4/2002 |

(Continued)

OTHER PUBLICATIONS

International Search Report mailed on Sep. 20, 2011, issued in PCT/JP2011/063447.

*Primary Examiner* — Monzer R Chorbaji
(74) *Attorney, Agent, or Firm* — Birch, Stewart, Kolasch & Birch, LLP

(57) ABSTRACT

A casing, including an inlet through which air can flow in and outlets through which air can flow out, is internally provided with: an air passage through which the inlet and the outlets are connected to each other; and an ion generation device for discharging ions into the air passage. The casing has an inclined wind guide surface and an attachment surface that forms an acute angle with the wind guide surface. The inlet is provided in a region of the wind guide surface, the distance of which from the attachment surface is shorter, the first outlet is provided in a region of the wind guide surface, the distance of which from the attachment surface is longer, and the second outlet is provided in a region of the casing, extending to the attachment surface from an end of the wind guide surface at which the first outlet is provided.

19 Claims, 24 Drawing Sheets

(56) References Cited

FOREIGN PATENT DOCUMENTS

| | | | |
|---|---|---|---|
| JP | 2003-59621 A | 2/2003 |
| JP | 2004-189147 A | 7/2004 |
| JP | 2004-309047 A | 11/2004 |
| JP | 2006-29665 A | 2/2006 |
| JP | 2007-21375 A | 2/2007 |

\* cited by examiner

ION GENERATOR AND AIR CLEANER

CROSS-REFERENCE TO RELATED APPLICATIONS

This application is the national phase under 35 U.S.C. §371 of PCT International Application No. PCT/JP2011/63447 which has international filing date of Jun. 13, 2011 and designated the United States of America.

The present invention relates to ion generators and air cleaners placed adjacent to discharge ports of air blowers provided on places such as walls.

BACKGROUND AND SUMMARY

In recent years, air cleaners for cleaning air in living space by ions have been put to practical use. In an air cleaner, an ion generation device for generating positive and negative ions is provided inside an air-blowing passage through which air sucked from outside by an air blower flows, and the generated ions are discharged outside together with air to be discharged. The discharged ions inactivate airborne articles in living space such as the interior of a room, kill floating bacteria (such as mold fungi), and change properties of odorous components. As a result, air in living space is cleaned.

Japanese Patent Application Laid-Open No. 2006-29665 discloses a "ceiling-embedded" air conditioner including a plasma generation device (ion generation device) in an indoor unit. The plasma generation device generates substances such as ions, ozone and hydroxyl radicals to decompose odorous components, fungi and viruses and render them harmless.

A conventional ceiling-embedded air conditioner having an air cleaning function incorporates an ion generation device in advance. When an ion generation device is provided in a ceiling-embedded air conditioner incorporating no ion generation device, the ceiling-embedded air conditioner that has already been placed must be extensively modified.

The present invention has been made in view of the above-described circumstances, and its object is to provide an ion generator and an air cleaner capable of efficiently diffusing ions into living space by utilizing wind generated by an air blower of an air conditioner, for example, provided on a place such as a wall, without modifying the air blower.

The present invention provides an ion generator including a casing that includes: an inlet through which air can flow in from outside; and an outlet through which air can flow out to outside, the casing being internally provided with: an air passage through which the inlet and the outlet are connected to each other; and an ion generation device for discharging ions into the air passage, wherein the casing has, at its outer surface, an inclined wind guide surface, and the inlet is provided at the wind guide surface.

In the present invention, air sent from outside is blown against the inclined wind guide surface at the outer surface of the casing, and flows along the wind guide surface; in addition, part of the air flows into the casing through the inlet provided in the wind guide surface, and the ions discharged into the air passage from the ion generation device are added to the part of the air when it flows through the air passage, so that ion-containing air flows out to outside through the outlet.

One aspect of the present invention provides the ion generator, wherein the casing includes another outer surface that forms an acute angle with the wind guide surface and serves as an attachment surface for an attachment target, wherein the inlet is provided in a region of the wind guide surface, the distance of which from the attachment surface is shorter, wherein a first outlet is provided in a region of the wind guide surface, the distance of which from the attachment surface is longer, wherein a second outlet is provided in a region of the casing at which an end of the wind guide surface provided with the first outlet is connected to the attachment surface, wherein the air passage is internally provided with a guide portion by which part of air flowing from the inlet toward the second outlet is guided to the first outlet, and wherein the ion generation device is provided closer to the inlet than the guide portion.

In the present invention, the attachment surface, i.e., another outer surface of the casing, which forms an acute angle with the wind guide surface, is attached to the attachment target. When air sent from an external air blower in a direction along the attachment surface is blown against the inclined wind guide surface from the region thereof, the distance of which from the attachment surface is shorter, toward the region thereof, the distance of which from the attachment surface is longer, the air flows along the wind guide surface; in addition, part of the air flows into the casing through the inlet provided in the region of the wind guide surface, the distance of which from the attachment surface is shorter, to flow through the air passage, and the ions discharged from the ion generation device are added to the part of the air when it flows through the air passage. The ion-containing air flows toward the second outlet provided in the region of the casing through which the end of the wind guide surface having the first outlet located in the region of the wind guide surface, the distance of which from the attachment surface is longer, is connected to the attachment surface, and then flows out to outside through the second outlet. Part of the air flowing toward the second outlet is guided toward the first outlet by the guide portion provided inside the air passage, and flows out to outside through the first outlet to merge with the air flowing along the wind guide surface.

Another aspect of the present invention provides the ion generator, wherein each of the inlet and the first outlet is a slit opening extended in parallel with a direction in which the region of the wind guide surface, the distance of which from the attachment surface is shorter, and the region of the wind guide surface, the distance of which from the attachment surface is longer, are connected to each other, and a plurality of the slit openings are arranged in a direction intersecting the direction in which the region of the wind guide surface, the distance of which from the attachment surface is shorter, and the region of the wind guide surface, the distance of which from the attachment surface is longer, are connected to each other, and wherein the inlet and the first outlet are located in the same position in the arrangement direction.

In the present invention, the inlets and the first outlets (which form the plurality of slit openings arranged in the direction intersecting the direction in which the region of the wind guide surface, the distance of which from the attachment surface is shorter, and the region of the wind guide surface, the distance of which from the attachment surface is longer, are connected to each other) are located in the same positions in the arrangement direction. Therefore, air, which flows into the casing through the inlet and to which the ions are added when the air flows through the air passage, is allowed to flow out to outside smoothly from the first outlet located in the same position as the inlet in the arrangement direction; in addition, when the air flows out to outside, the air is merged with air stably flowing along regions of the wind guide surface on both sides of the inlet and the first outlet, i.e., the slit opening, where no opening is formed, and is thus efficiently diffused into external space.

Still another aspect of the present invention provides the ion generator, wherein the inlet and the first outlet are continuous with each other in a direction in which the region of the wind guide surface, the distance of which from the attachment surface is shorter, and the region of the wind guide surface, the distance of which from the attachment surface is longer, are connected to each other, so that the inlet and the first outlet form a slit opening extended in parallel with the direction in which the inlet and the first outlet are continuous with each other, and a plurality of the slit openings are arranged in a direction intersecting the direction in which the region of the wind guide surface, the distance of which from the attachment surface is shorter, and the region of the wind guide surface, the distance of which from the attachment surface is longer, are connected to each other.

In the present invention, the inlet and the first outlet (which are arranged in the direction intersecting the direction in which the region of the wind guide surface, the distance of which from the attachment surface is shorter, and the region of the wind guide surface, the distance of which from the attachment surface is longer, are connected to each other) are continuous with each other so as to form the single slit opening. Therefore, the ratio between openings serving as the inlets and openings serving as the first outlets is suitably changed in accordance with, for example, flow rate, flow velocity and direction of air flowing along the wind guide surface.

Further, air, which flows into the casing through the slit opening serving as the inlet and to which the ions are added when the air flows through the air passage, is allowed to flow out to outside smoothly from the first outlet of the same slit opening; in addition, when the air flows out to outside, the air is merged with air stably flowing along regions of the wind guide surface on both sides of the slit opening, where no opening is formed, and is thus efficiently diffused into external space.

Yet another aspect of the present invention provides the ion generator, wherein a width of each of a plurality of the slit openings in the arrangement direction thereof is wider than a distance between ends of the slit openings adjacent to each other in the arrangement direction thereof.

In the present invention, since the proportion of the inlets and the first outlets, serving as the slit openings, in the wind guide surface is large, the amount of air flowing into the casing and flowing out to outside is increased, thus making it possible to discharge a larger amount of ions into a room.

Still yet another aspect of the present invention provides the ion generator, wherein the guide portion is a plate piece protruded from an inner surface of the casing toward an inner region of the air passage.

In the present invention, the guide portion can be easily formed by erecting the plate piece on the inner surface of the casing.

Another aspect of the present invention provides the ion generator, wherein the ion generation device has an ion generation part for discharging ions toward opposite to the attachment surface.

In the present invention, the ion generation part for discharging ions toward opposite to the attachment surface can efficiently discharge ions to air that is sent in the direction along the attachment surface so as to be blown against the wind guide surface and flows into the casing through the inlet so as to flow through the air passage along the attachment surface.

The present invention provides an air cleaner for cleaning air discharged from a discharge port of an air conditioner placed on a ceiling, wherein the air cleaner includes: a main body having an ion generation part for discharging ions for cleaning air discharged from the discharge port; and attachment means for fixing the main body to a region of a ceiling surface located downstream of the discharge port.

In the present invention, the main body of the air cleaner is placed downstream of the given discharge port of the air conditioner by using the attachment means such as a screw, thus making it possible to clean the air discharged from the given discharge port and to supply the cleaned air toward a given area of the interior of a room.

Furthermore, the main body is placed downstream of the given discharge port of the air conditioner, and thus the air cleaner can be more easily used in combination with an existing air conditioner as compared with a case where the main body is placed inside the air conditioner Another aspect of the present invention provides the air cleaner, wherein the main body preferably has: a seating to which the ion generation part is fixed; and a cover for covering the ion generation part, and wherein the cover is preferably provided with: an introduction port through which air discharged from the discharge port of the air conditioner is introduced; and an outlet through which the ions are discharged together with the air introduced to inside of the cover from the introduction port.

In the present invention, the cover having the introduction port and the outlet covers the ion generation part, thereby making it possible to protect the ion generation part and to allow the air cleaned by the ions and flow of the ions to be discharged from the outlet in a given direction.

Still another aspect of the present invention provides the air cleaner, wherein the main body preferably includes at least one spacer interposed between the seating and the ceiling surface, and wherein the attachment means preferably includes: a seating fixation member for fixing the seating to the spacer; and a spacer fixation member for fixing the spacer to the ceiling surface.

In the present invention, one or a plurality of the spacers are interposed between the seating and the ceiling surface, thus making it possible to perform positioning of the introduction port of the cover in accordance with position and/or wind direction of the discharge port.

Yet another aspect of the present invention provides the air cleaner, wherein the spacer fixation member is preferably a screw, wherein the spacer preferably has a screw hole through which the screw for fixing the spacer to the ceiling surface is inserted, and wherein the seating is preferably provided with an opening so that a planar location of the opening and that of the screw hole of the spacer correspond to each other.

In the present invention, the seating or the spacer can be screwed to the ceiling surface at the same position. In other words, the spacer can be selectively used. Accordingly, at a given position of the ceiling surface, an anchor is embedded in a ceiling in advance, for example, so that an attachment position for the screw is formed; then, the seating or the spacer can be screwed to the ceiling surface at the attachment position where a shared anchor, for example, is located.

Still yet another aspect of the present invention provides the air cleaner, wherein the air cleaner preferably further includes guide means provided inside the cover and opposite to the introduction port with respect to the ion generation part, the guide means guiding an air flow inside the cover downward.

In the present invention, the air cleaned inside the cover can be smoothly guided downward by the guide means. Thus, the amount of the cleaned air supplied to the given area can be increased.

Another aspect of the present invention provides the air cleaner, wherein the guide means is preferably molded integrally with the cover by filling part of the outlet of the cover.

In the present invention, the air cleaned inside the cover can be smoothly guided downward by the guide means formed integrally with the cover. Besides, since the guide means is formed by an inner peripheral surface of the cover, the cover and the guide means are extremely easily molded.

Still another aspect of the present invention provides the air cleaner, wherein the cover is preferably openable by being rotated in a direction in which the cover moves away from the air conditioner.

In the present invention, the cover can be opened by being rotated in a direction in which the cover moves away from the air conditioner, thus making it possible to easily open and close the cover while preventing the cover from colliding with the air conditioner.

Yet another aspect of the present invention provides the air cleaner, wherein the cover preferably has: a cover main body; and a hinge portion protruded from the cover main body toward the seating, and wherein the hinge portion is preferably rotatably connected to the seating.

In the present invention, the cover is connected to the seating only through the hinge portion protruded from the cover main body, and thus the cover is easily detached.

Still yet another aspect of the present invention provides the air cleaner, wherein at an externally exposed outer peripheral surface of the seating, there is preferably formed a pull-out hole through which an electric wire for connection with the ion generation part is pulled out.

In the present invention, the electric wire can be pulled out from the outer peripheral surface of the seating through the pull-out hole formed at the outer peripheral surface of the seating. Hence, routing of the electric wire along the ceiling surface is considerably facilitated.

According to the present invention, air sent from an external air blower is blown against the inclined wind guide surface at the outer surface of the casing, and is allowed to flow along the wind guide surface, while part of the air is allowed to flow into the casing through the inlet provided in the wind guide surface, so that the ions are added to the part of the air flowing through the air passage inside the casing and then the resulting air is allowed to flow out to outside. Thus, there is provided the ion generator capable of efficiently diffusing the ions into living space by utilizing wind generated by an air blower of an air conditioner, for example, provided on a place such as a wall, without modifying the air blower.

Furthermore, according to the present invention, the two types of the outlets are provided in different regions of the casing so that part of air, which flows into the casing through the inlet provided in the wind guide surface and flows toward the second outlet after addition of the ions, is guided toward the first outlet by the guide portion provided at the wind guide surface, and the air flows out to outside through the first and second outlets. Thus, there is provided the ion generator capable of more efficiently diffusing the ions into living space.

The air cleaner according to the present invention is capable of supplying the cleaned air toward the given area of the interior of a room. Besides, the air cleaner according to the present invention is easily used in combination with an existing air conditioner.

DETAILED DESCRIPTION OF NON-LIMITING EXAMPLE EMBODIMENTS

Hereinafter, embodiments of ion generators and air cleaners according to the present invention will be described with reference to the drawings.

<Embodiment 1>

Figure 1:
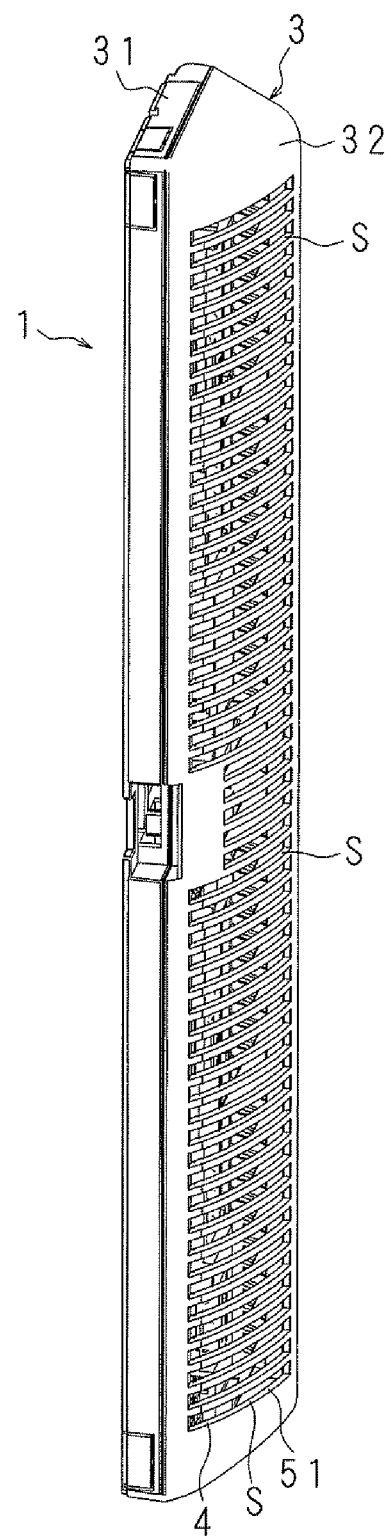
FIG. 1 is a perspective view of an ion generator according to Embodiment 1 of the present invention.
Figure 2:
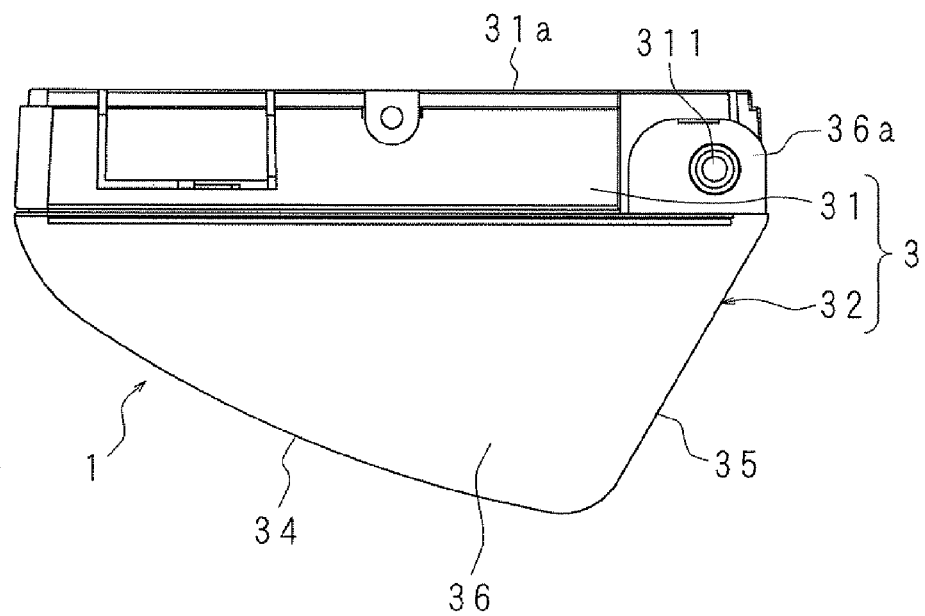
FIG. 2 is a lateral view of the ion generator illustrated in FIG. 1.
Figure 3:
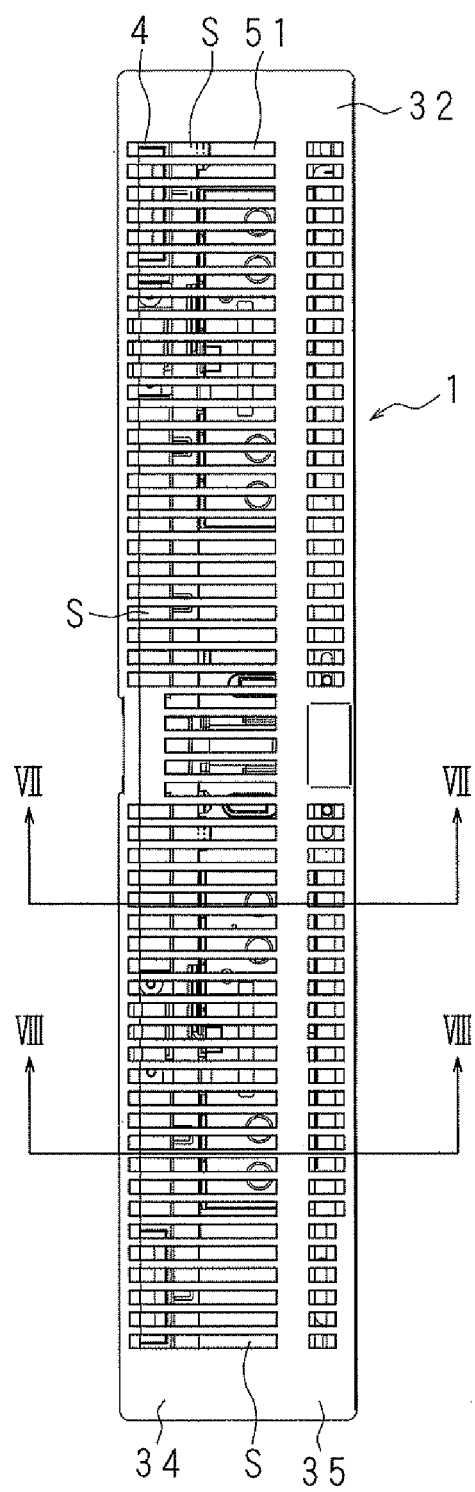
FIG. 3 is a bottom view of the ion generator illustrated in FIG. 1.
Figure 4:
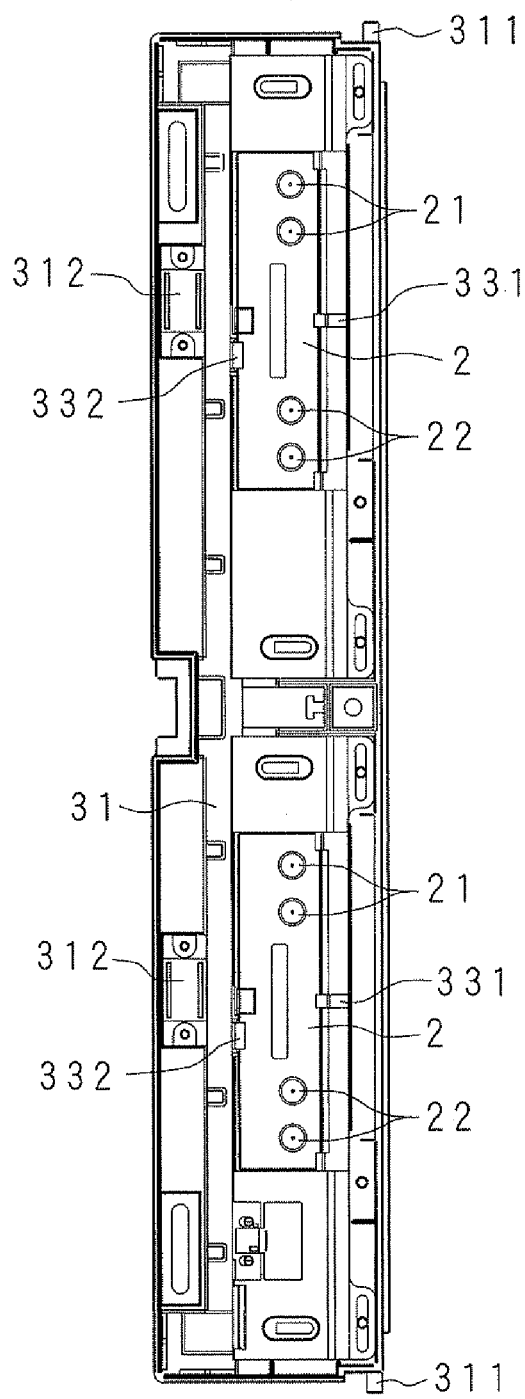
FIG. 4 is a bottom view of the ion generator illustrated in FIG. 1, from which its cover is removed.
Figure 5:
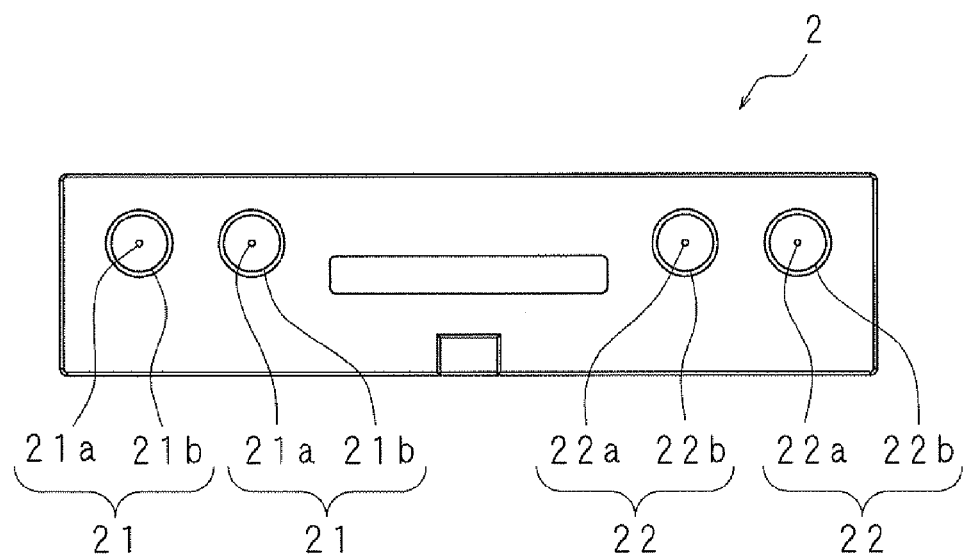
FIG. 5 is a plan view schematically illustrating an example of an ion generation device.
Figure 6:
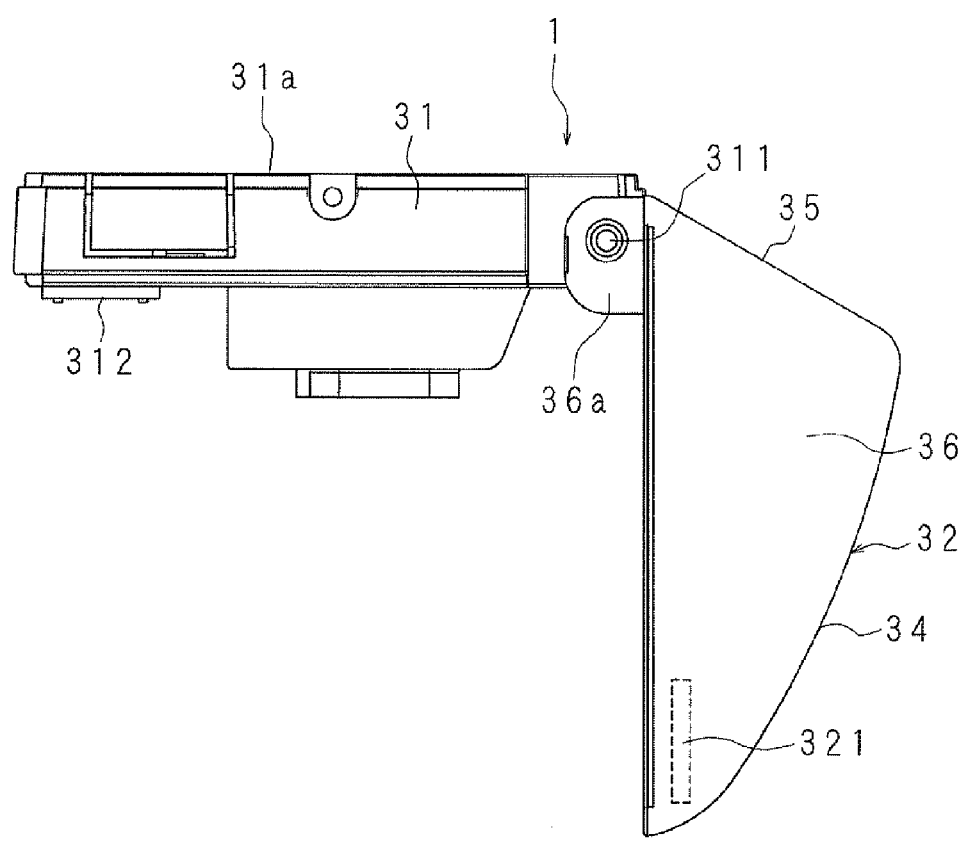
FIG. 6 is a lateral view of the ion generator of FIG. 1, with its cover opened.
Figure 7:
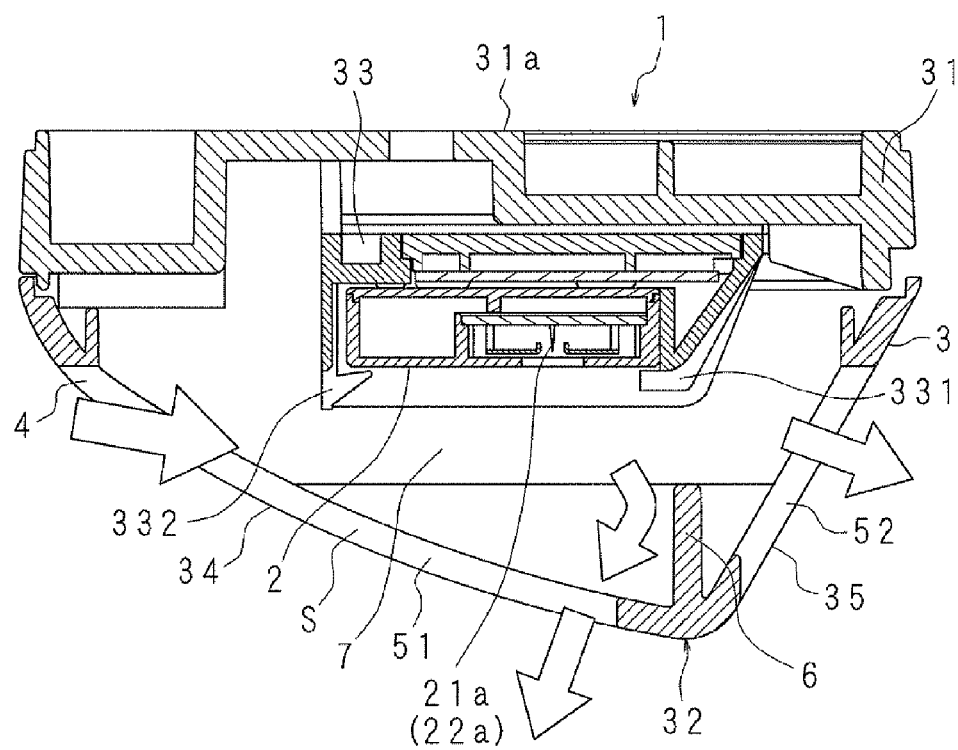
FIG. 7 is a lateral cross-sectional view taken along the line VII-VII of FIG. 3.
Figure 8:
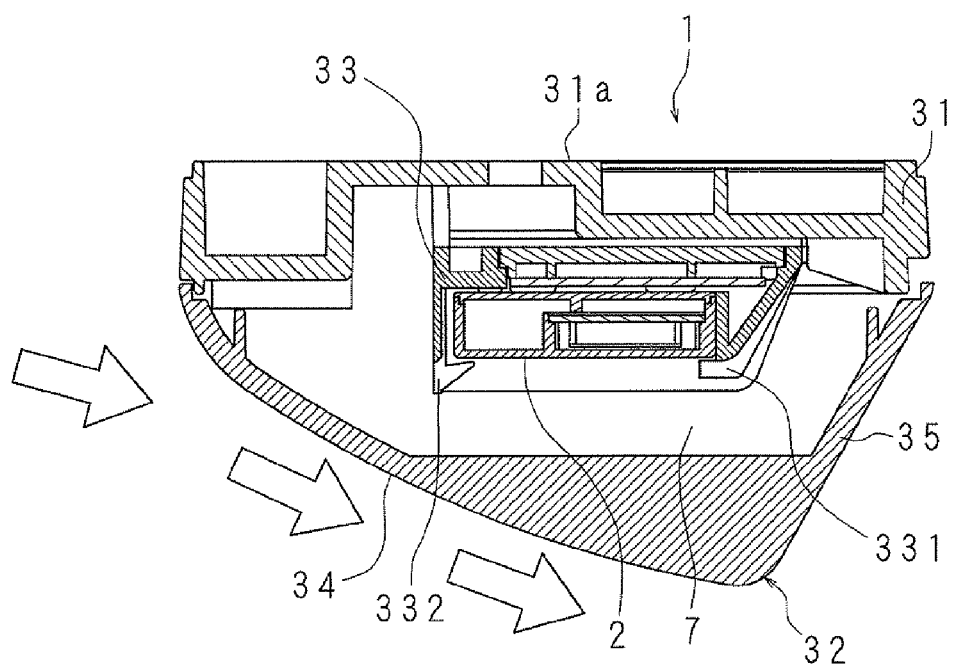
FIG. 8 is a lateral cross-sectional view taken along the line VIII-VIII of FIG. 3.

FIG. 1 is a perspective view of an ion generator according to Embodiment 1 of the present invention. FIG. 2 is a lateral view of the ion generator illustrated in FIG. 1. FIG. 3 is a bottom view of the ion generator illustrated in FIG. 1. FIG. 4 is a bottom view of the ion generator illustrated in FIG. 1, from which its cover is removed. FIG. 5 is a plan view schematically illustrating an example of an ion generation device. FIG. 6 is a lateral view of the ion generator of FIG. 1, with its cover opened. FIG. 7 is a lateral cross-sectional view taken along the line VII-VII of FIG. 3. And FIG. 8 is a lateral cross-sectional view taken along the line VIII-VIII of FIG. 3. Note that FIGS. 7 and 8 each illustrate structure and operation of the ion generator of FIG. 1.

An ion generator 1 according to the present invention includes a casing 3 having: an approximately cuboid base 31 elongated in one direction; and a cover 32 for covering the base 31 from below. Note that an upper surface of the base 31 of the ion generator 1 according to the present invention is attached to an attachment target such as a ceiling so that the cover 32 is located under the base 31 as described later, and therefore, the upper surface of the base 31 is defined as an attachment surface 31a.

The base 31 is provided at its lower surface with two longitudinally-spaced fixation members 33 for fixing two approximately cuboid ion generation devices 2. Each fixation member 33 includes: an undeformable hook-like first engagement portion 331; and a deformable second engagement portion 332 having a hook at its end. The first and second engagement portions 331 and 332 are engaged with lateral surfaces and lower edges of the ion generation devices 2.

Each ion generation device 2 includes four ion generation parts 21 and 22. Each ion generation part 21 has: a needle-like discharge electrode 21a; and an induction electrode ring 21b surrounding the discharge electrode 21a, and the discharge electrode 21a is located at a center of a region surrounded by the induction electrode ring 21b. Each ion generation part 22 has: a needle-like discharge electrode 22a; and an induction electrode ring 22b surrounding the discharge electrode 22a, and the discharge electrode 22a is located at a center of a region surrounded by the induction electrode ring 22b. There is provided a power supply (not illustrated) for supplying a voltage to each of the ion generation parts 21 and 22, and a voltage is supplied from the power supply to each of the ion generation parts 21 and 22, thereby causing the ion generation parts 21 and 22 to generate ions.

As will be described below, the ion generation parts 21 generate positive ions, while the other ion generation parts 22 generate negative ions.

Voltages are applied to the ion generation parts 21 so that the discharge electrodes 21a become positive, and water molecules in air are electrolyzed in discharge-induced plasma regions, thereby mainly generating hydrogen ions H. Then, water molecules in air gather around the generated hydrogen ions $H^+$, thereby creating positive cluster ions $H^+(H_2O)m$ (where m is any integer), which will hereinafter be referred to as "positive ions". Voltages are applied to the other ion generation parts 22 so that the discharge electrodes 22a become negative, and oxygen molecules in air are electrolyzed in discharge-induced plasma regions, thereby mainly generating oxygen ions $O_2^-$. Then, water molecules in air gather around the generated oxygen ions $O_2^-$, thereby creating negative cluster ions $O_2^-(H_2O)n$ (where n is any integer), which will hereinafter be referred to as "negative ions".

In the present embodiment, the ion generation device 2 including the ion generation parts 21 for generating positive ions and the ion generation parts 22 for generating negative ions is used, but an ion generation device for generating only negative ions or an ion generation device for generating other ions may alternatively be used. Further, polarities of ions generated by the ion generation parts 21 and 22 of the ion generation device 2 may be changed for each given period of time.

The cover 32 has an approximately inverted triangle shape in side view, and is elongated along a longitudinal direction of the base 31. The cover 32 includes a plate material that forms: first and second inclined surfaces 34 and 35 corresponding to two sides of the inverted triangle; and lateral surfaces 36 located at ends of the first and second inclined surfaces 34 and 35.

In the wind guide surface (i.e., the first inclined surface) 34, a plurality of slit openings S are formed (arranged) along a longitudinal direction of the cover 32. Widths of the slit openings S in the arrangement direction thereof are wider than distances between ends of the slit openings S adjacent to each other in the arrangement direction thereof. One region of each slit opening S (i.e., a region of each slit opening S, the distance of which from the attachment surface 31a is shorter) serves as an inlet 4, and the other region of each slit opening S (i.e., a region of each slit opening S, the distance of which from the attachment surface 31a is longer) serves as a first outlet 51. In other words, in the present embodiment, the inlet 4 and the first outlet 51 constitute the single continuous slit opening S.

Further, the second inclined surface 35, serving as a casing region through which an end of the wind guide surface 34 and the attachment surface 31a are connected to each other, includes slit second outlets 52. Note that the shape of each second outlet 52 is not limited to a slit shape, but a single or a plurality of rectangular openings, for example, may be formed as the second outlet(s) 52.

A lower surface of the base 31 and an inner wall surface of the cover 32 constitute an air passage 7 through which the inlets 4 and the first and second outlets 51 and 52 are connected to each other. At a top of the inverted triangle connecting the first and second inclined surfaces 34 and 35, there is provided a wind barrier plate 6 which is extended approximately vertically upward from an inner side of the cover 32 into the air passage 7 and along which an air flow flowing in through the inlets 4 is guided to the first outlets 51. The wind barrier plate 6 is formed so as to be elongated along the longitudinal direction of the cover 32. Note that the wind barrier plate 6 does not necessarily have to be formed into a vertically upwardly extended shape, but may be formed into any other shape as long as it guides wind to the first outlets 51.

From upper regions of the lateral surfaces 36 of the cover 32, ear portions 36a provided with holes are extended. At the same time, longitudinal ends of the base 31 are provided with a fulcrum shaft 311. The fulcrum shaft 311 of the base 31 fits into the holes of the ear portions 36a of the cover 32, thus allowing the cover 32 to be rotated around the fulcrum shaft 311 relative to the cover 32. FIG. 6 is a lateral view of the ion generator 1, with the cover 32 opened downward by 90°.

An end of the base 31, located opposite to the fulcrum shaft 311, is provided with magnets 312, and the cover 32 is provided with magnets 321 located at positions corresponding to those of the magnets 312 of the base 31. When the cover 32 is closed, the magnets 321 of the cover 32 and the magnets 312 of the base 31 attract each other, thereby making it possible to maintain the closed state of the cover 32. The cover 32 is rotatable as described above, thus making it possible to easily change and clean the ion generation devices 2.

Note that the magnets are provided at positions that do not overlap with the ion generation parts 21 and 22 of the ion generation devices 2 in a longitudinal direction of the ion generator 1. The magnets are provided in this manner in order to prevent the ions from being attracted by the magnets and prevent a reduction in ion concentration to the extent possible.

Figure 9:
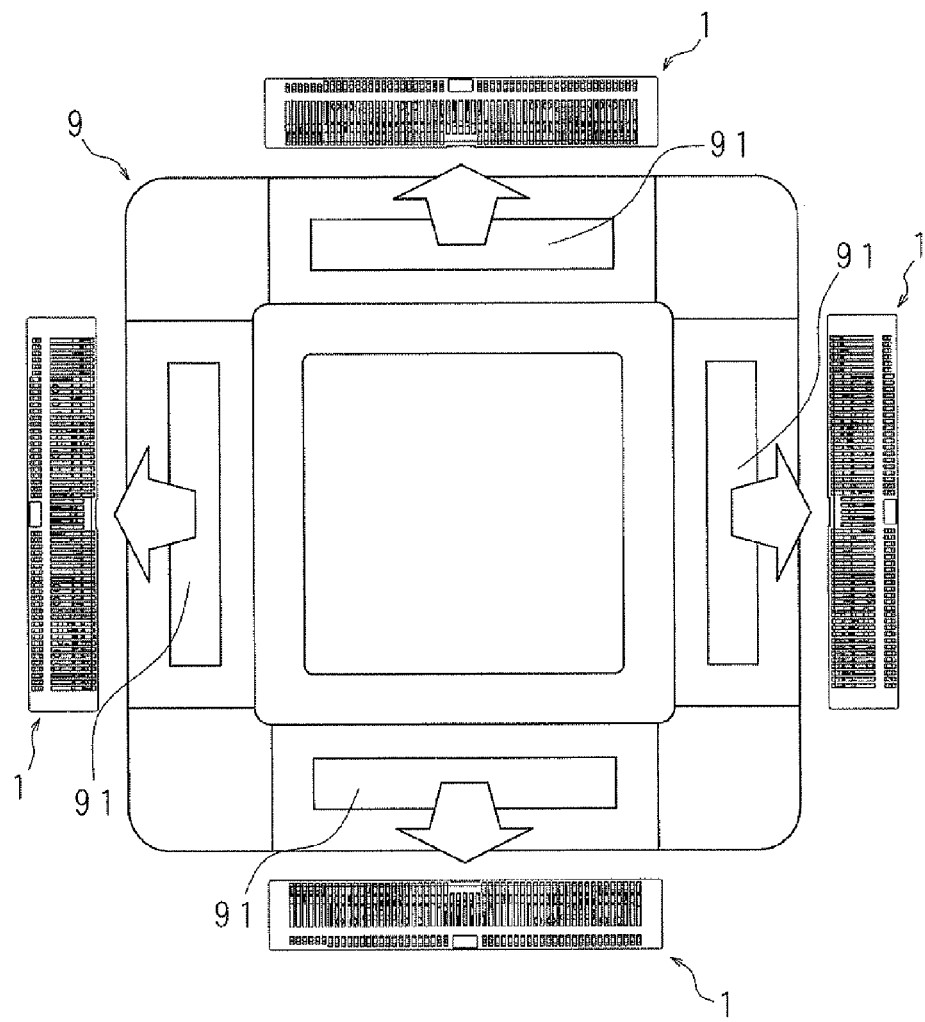
FIG. 9 is a plan view of a ceiling region, illustrating how each ion generator illustrated in FIG. 1 is placed and operated.
Figure 10:
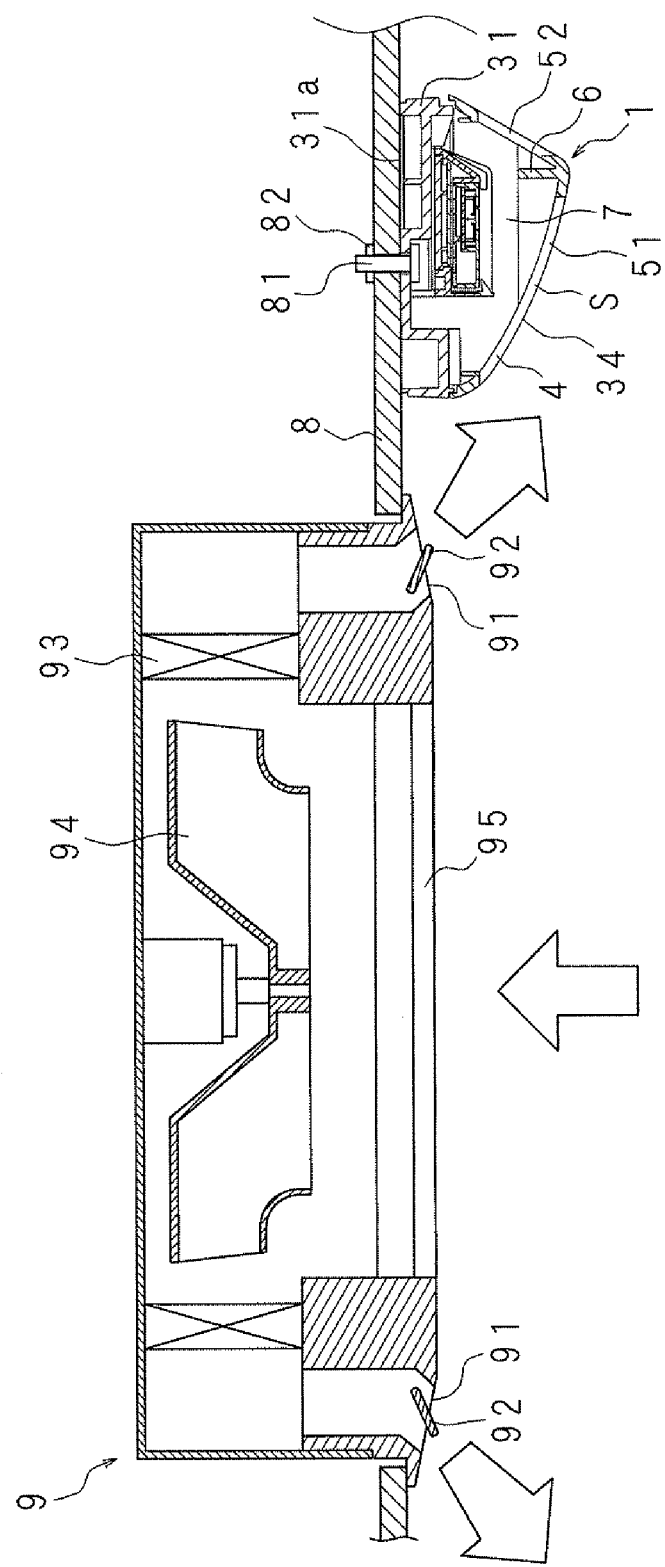
FIG. 10 is a lateral cross-sectional view of the ceiling region, illustrating structure and operation of the placed ion generator of FIG. 1.

Next, how the ion generator 1 according to the present embodiment is placed will be described. FIG. 9 is a plan view of a ceiling region, illustrating how each ion generator illustrated in FIG. 1 is placed and operated, and FIG. 10 is a lateral cross-sectional view of the ceiling region, illustrating structure and operation of the placed ion generator of FIG. 1.

The ion generators 1 according to the present embodiment are placed on a ceiling 8 so as to be located in the vicinity of discharge ports 91 of a ceiling-embedded air conditioner 9. The ceiling-embedded air conditioner 9 includes the four discharge ports 91 from which air is discharged in four directions. Each ion generator 1 is placed for the associated discharge port 91 of the ceiling-embedded air conditioner 9 so that the first inclined surface 34 is located close to the discharge port 91. Note that since a lighting apparatus, for example, may have already been placed on the ceiling 8, it is not always possible to place the ion generators 1 for all the discharge ports 91, and therefore, the ion generators 1 may be placed for only some of the discharge ports 91.

Each ion generator 1 is attached and fixed in the vicinity of a region of the ceiling 8 where the ceiling-embedded air conditioner 9 is placed so that the attachment surface 31a of an upper side of the base 31 faces a wall of the ceiling 8. Each ion generator 1 is fixed with the use of a fixation bolt 81. The fixation bolt 81 is passed through a hole provided in the base 31 and a hole provided in the ceiling 8 from the base 31, and is fixed by a nut 82 at a back surface of the ceiling.

The ceiling-embedded air conditioner 9 includes: an inlet 95; an air blower 94; a heat exchanger 93; and the discharge ports 91. During operation of the ceiling-embedded air conditioner 9, air inside a room is sucked through the inlet 95 by the air blower 94 and passed through the heat exchanger 93, and thus conditioned air is discharged from the discharge ports 91. The discharge ports 91 are each equipped with a wind direction changing plate 92.

The ceiling-embedded air conditioner 9 discharges the conditioned air toward the wind guide surface (i.e., the first inclined surface) 34 of the ion generator 1. As indicated by the arrows, the discharged conditioned air flows along the wind guide surface 34. Furthermore, as indicated by the arrow in FIG. 7, through a region of the wind guide surface 34 where the inlet 4 is located, the conditioned air flows into the air passage 7 inside the ion generator 1 from the inlet 4.

In this embodiment, the ions generated by the ion generation devices 2 are discharged downward from the ion generation parts 21 and 22 of the ion generation devices 2 by ion wind. When the conditioned air flowing from the inlets 4 flows through the air passage 7, the ions generated by the ion generation devices 2 are added to the conditioned air, and the resulting air is discharged outside of the ion generator 1 from the first and second outlets 51 and 52.

Part of the conditioned air containing the ions is blown against the wind barrier plate 6 and guided toward the first outlets 51, and then flows out from the first outlet 51. The ion-containing conditioned air, flowing out from the first outlets 51, is merged with the conditioned air flowing along the wind guide surface 34, and the resulting air is discharged into the room. Further, the remaining ion-containing conditioned air flows out from the second outlets 52. The ion-containing conditioned air flowing out from the first outlets 51 and the ion-containing conditioned air flowing out from the second outlets 52 allow the ions to be efficiently diffused into the room.

As described above, the inclined wind guide surface 34 is provided with the inlets 4; thus, the conditioned air, discharged from the discharge port 91 of the ceiling-embedded air conditioner 9 so as to flow along the wind guide surface 34, can be divided into: air flowing along the inclined wind guide surface 34; and air flowing into the ion generator 1 through the inlets 4 of the ion generator 1.

Furthermore, the first outlets 51 are provided in regions of the wind guide surface 34 located downstream of the inlets 4 with respect to a flowing direction of the conditioned air discharged from the discharge port 91 of the ceiling-embedded air conditioner 9, thus allowing part of air, which flows into the ion generator 1 and to which the ions are added, to flow out from the first outlets 51 and to merge into air flowing along the wind guide surface 34 again.

In Embodiment 1, the slit openings S in which the inlets 4 and the first outlets 51 are continuous with each other are formed; therefore, the ratio between a region of each slit opening S, serving as the inlet 4, and a region of each slit opening S, serving as the first outlet 51, can be changed in accordance with, for example, flow rate, flow velocity and direction of the conditioned air flowing along the first inclined surface 34. When the proportion of the region of each slit opening S, serving as the inlet 4, is increased, the amount of air flowing into the ion generator 1 is increased; hence, ions are added to the air inside the ion generator 1, and the air containing a larger amount of ions is allowed to flow out to outside from the first and second outlets 51 and 52.

The ratio between the amount of the conditioned air flowing out from the first outlets 51 and that of the conditioned air flowing out from the second outlets 52 can be changed by adjusting a length of the wind barrier plate 6. When the length of the wind barrier plate 6 is increased, the proportion of air quantity of the conditioned air flowing out from the first outlets 51 is increased, and when the length of the wind barrier plate 6 is reduced, the proportion of air quantity of the conditioned air flowing out from the first outlets 51 is reduced.

Figure 11:
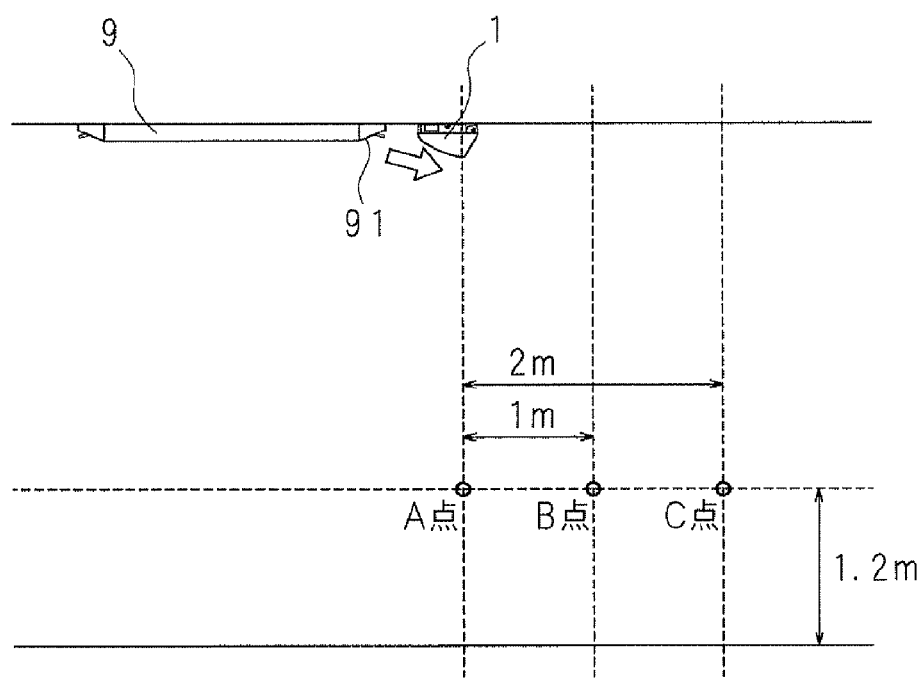
FIG. 11 is a diagram illustrating locations of measurement points at which ion diffusion effects of the ion generator of FIG. 1 are measured.

Influence exerted on an ion concentration distribution in a room by the wind barrier plate 6 in the present embodiment is demonstrated in Table 1. FIG. 11 is a diagram illustrating locations of measurement points at which ion diffusion effects of the ion generator of FIG. 1 are measured. The ion generator 1 was placed on a region of a ceiling located in the vicinity of the discharge port 91 of the ceiling-embedded air conditioner 9. Note that a height of the wind barrier plate 6 was 10 mm. The ceiling-embedded air conditioner 9 was operated under given conditions (operation mode: cooling, set temperature: 28° C., and air quantity: large), with the wind direction changing plate 92 of the ceiling-embedded air conditioner 9 being put in a most upward position. A position located at a height of 1.2 m from a floor surface and directly vertically below the ion generator 1 was set as a point A, a position located at a height of 1.2 m from the floor surface and horizontally away from the ion generator 1 by 1 m was set as a point B, and a position located at a height of 1.2 m from the floor surface and horizontally away from the ion generator 1 by 2 m was set as a point C.

At each of the positions of the points A, B and C, measurements were made on positive ion and negative ion concentrations when the wind barrier plate 6 is provided in the ion generator 1 and when no wind barrier plate 6 is provided. In Table 1, numeric values with + represent positive ion concentrations, and numeric values with − represent negative ion concentrations. Rates of changes in Table 1 each represent the ratio of the ion concentration obtained by the ion generator provided with the wind barrier plate 6 to the ion concentration obtained by the ion generator provided with no wind barrier plate 6. As indicated by Table 1, the ion concentration obtained by the ion generator provided with the wind barrier plate 6 was higher than the ion concentration obtained by the ion generator provided with no wind barrier plate 6 by 25% to 92%.

TABLE 1

|  |  | ION CONCENTRATION [ions/cm$^3$] | | | | | |
|---|---|---|---|---|---|---|---|
| NO WIND BARRIER IS PROVIDED |  | A | +6000<br>−7000 | B | +6000<br>−6000 | C | +7000<br>−8000 |
| WIND BARRIER IS PROVIDED |  | A | +7500<br>−9000 | B | +9000<br>−11500 | C | +10500<br>−15000 |
| RATES OF CHANGES | POSITIVE ION |  | 125% |  | 150% |  | 150% |
|  | NEGATIVE ION |  | 129% |  | 192% |  | 188% |

As described above, when the wind barrier plate 6 is provided, ion-containing air discharged from the first outlets 51 can be merged with air flowing along the wind guide surface 34 and diffused into a room; hence, the ion generator provided with the wind barrier plates 6 is capable of diffusing the ions into a room more efficiently than the ion generator provided with no wind barrier plate 6.

Note that when the ion generator 1 is provided with no second outlet 52, escape of air flowing from the inlets 4 (i.e., outflow of the air to outside) is reduced, thus reducing the conditioned air flowing into the ion generator 1; accordingly, the ions generated inside the ion generator 1 cannot be efficiently diffused into a room.

<Embodiment 2>

Figure 12:
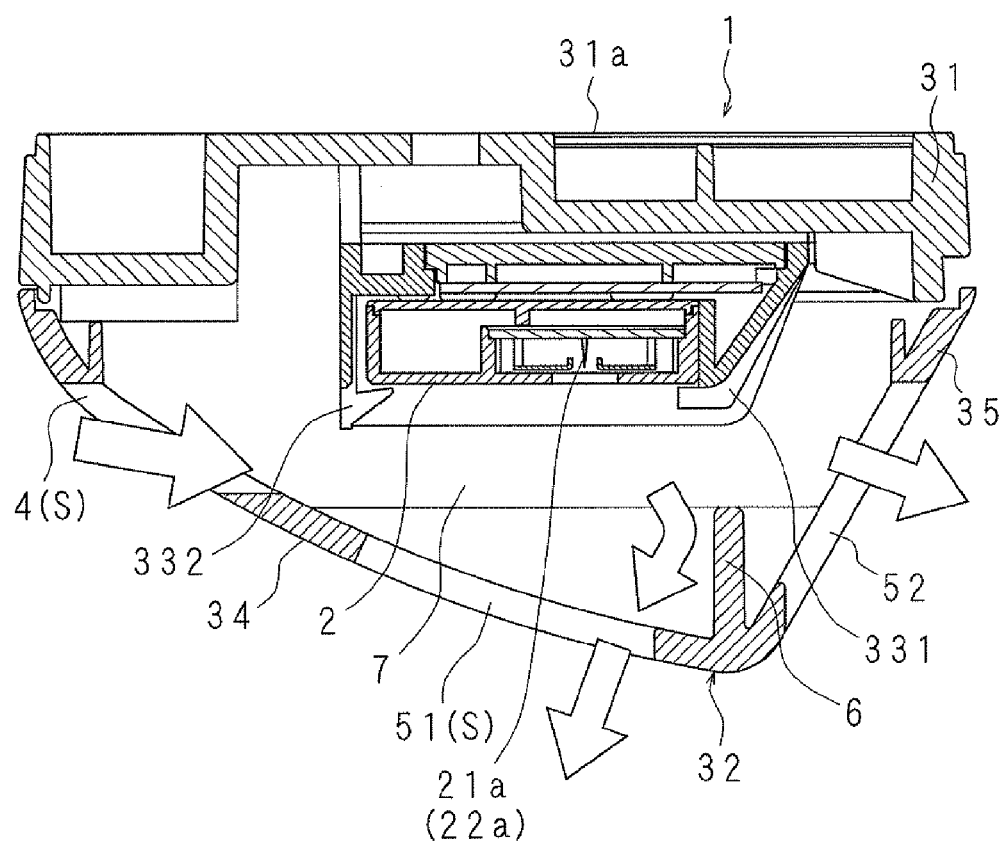
FIG. 12 is a lateral cross-sectional view of an ion generator according to Embodiment 2 of the present invention.

FIG. 12 is a lateral cross-sectional view of an ion generator according to Embodiment 2 of the present invention. Embodiment 2 differs from Embodiment 1 in that the inlets 4 and the first outlets 51 are not continuous with each other and serve as separate slit openings S.

In Embodiment 2, an area of each inlet 4 provided in the wind guide surface 34 is adjusted, thereby enabling adjustment of the amount of air flowing into the ion generator 1. When the area of each inlet 4 is increased, the amount of air flowing into the ion generator 1 is increased, and therefore, a larger amount of ions can be generated inside the ion generator 1.

In Embodiments 1 and 2 described above, the ion generators 1 according to the present invention are placed on regions of the ceiling 8 located in the vicinity of the discharge ports 91 of the ceiling-embedded air conditioner 9, but an apparatus to which the present invention is applied is not limited to a ceiling-embedded air conditioner; alternatively, the present invention is applicable to an air blower placed on a wall surface.

<Embodiment 3>

Figure 13:
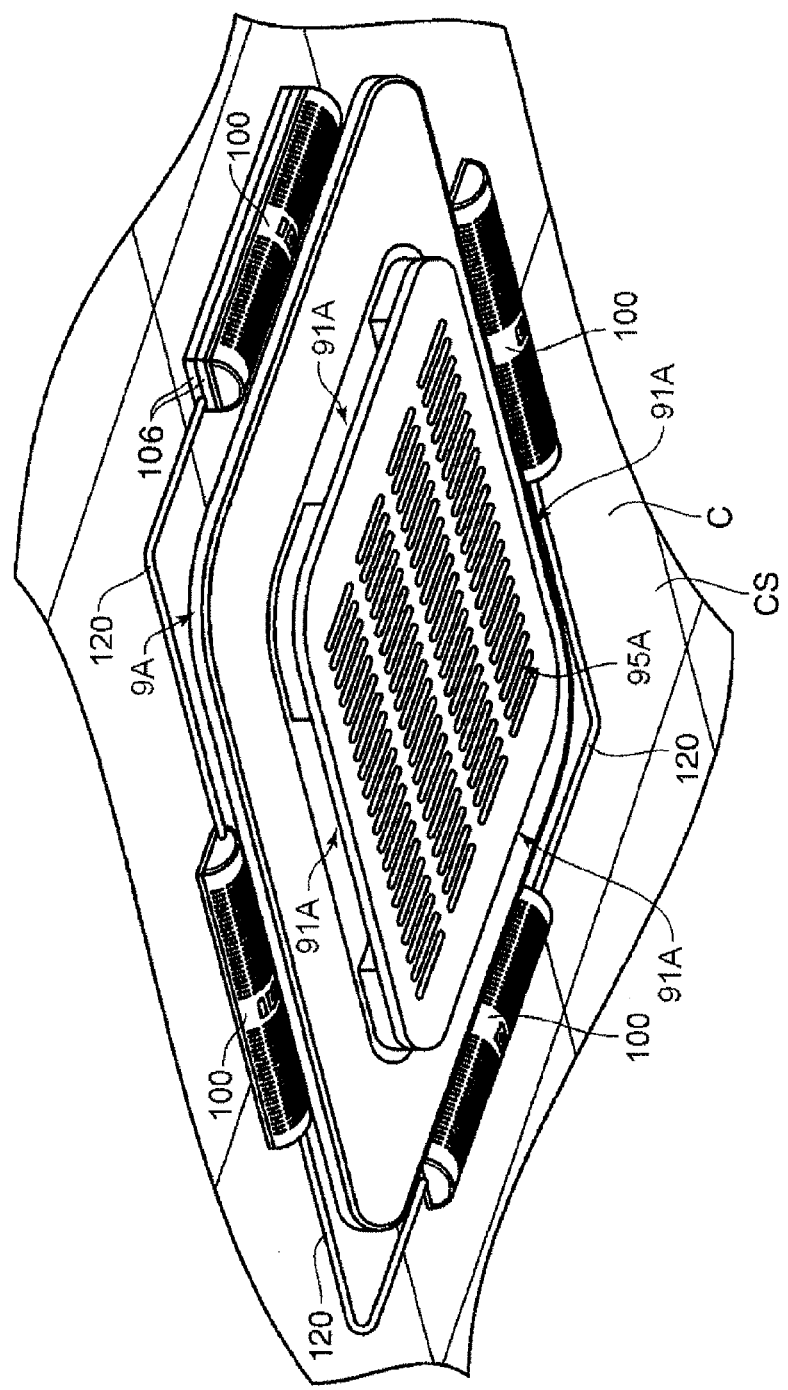
FIG. 13 is a perspective view of air cleaners according to Embodiment 3 of the present invention, placed around a ceiling-embedded air conditioner.

Air cleaners 100 according to Embodiment 3, illustrated in FIG. 13, clean air discharged from an air conditioner 9A placed on a ceiling surface CS of a ceiling C.

The air conditioner 9A has: discharge ports 91A opened in four directions along the ceiling surface CS; and intake ports 95A located at positions surrounded by the four discharge ports 91A and opened downward.

Each air cleaner 100 is placed forward of the associated discharge port 91A, and generates ions P to clean air discharged from the discharge port 91A.

The four air cleaners 100 illustrated in FIG. 13 are electrically connected to each other via a harness 120 routed along the ceiling surface CS. One of the four air cleaners 100 functions as a master unit, and an electric system extends therefrom to the other air cleaners 100 functioning as slave units via the harness 120 in a branched manner, thus making it possible to collectively control the four air cleaners 100. Note that the harness 120 covered with a molded cover made of a synthetic resin is routed along the ceiling surface CS.

Figure 14:
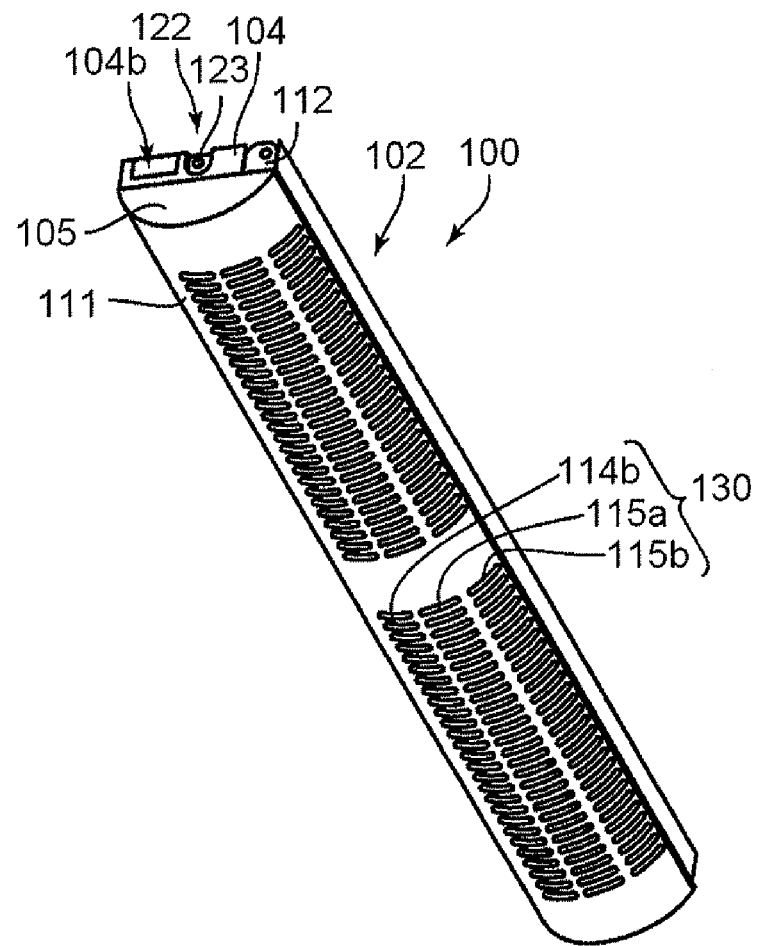
FIG. 14 is a perspective view of the air cleaner illustrated in FIG. 13.
Figure 15:
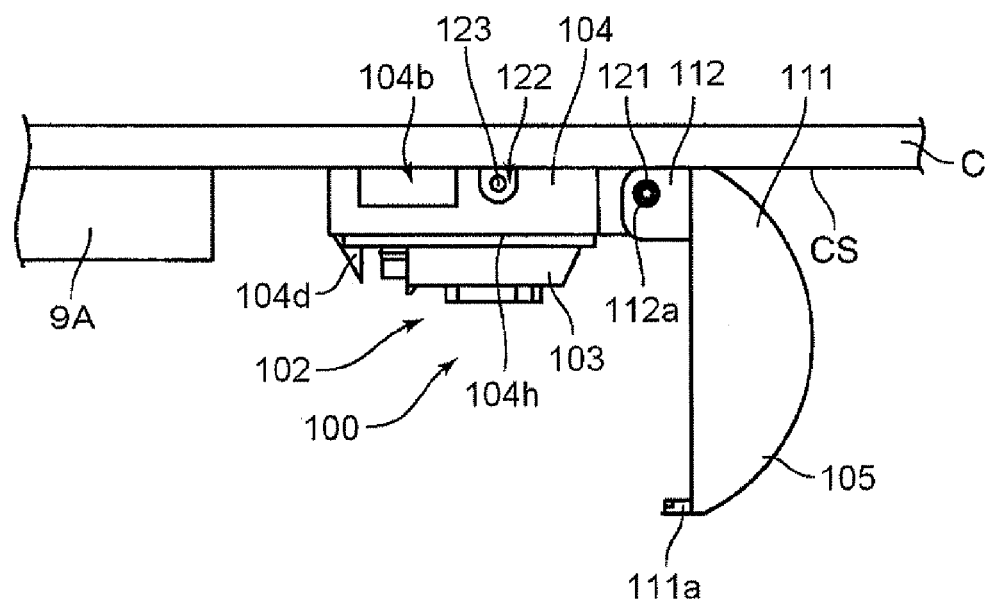
FIG. 15 is a lateral view of the air cleaner of FIG. 13, placed on a ceiling surface.
Figure 16:
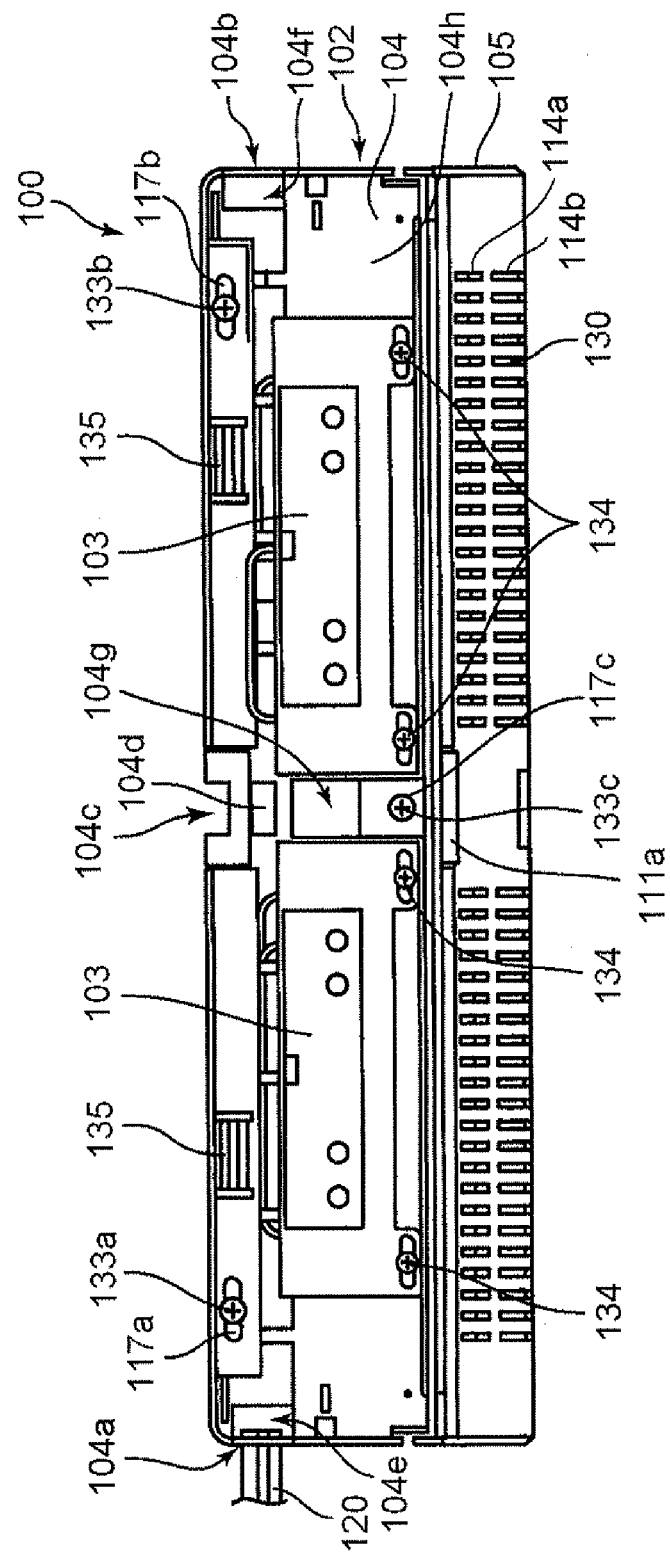
FIG. 16 is a plan view of the air cleaner of FIG. 13, with its cover opened.

As illustrated in FIGS. 14 to 16, the air cleaner 100 includes: a main body 102; and an attachment means for fixing the main body 102 to a region of the ceiling surface CS located downstream (i.e., forward) of the discharge port 91A.

Figure 19:
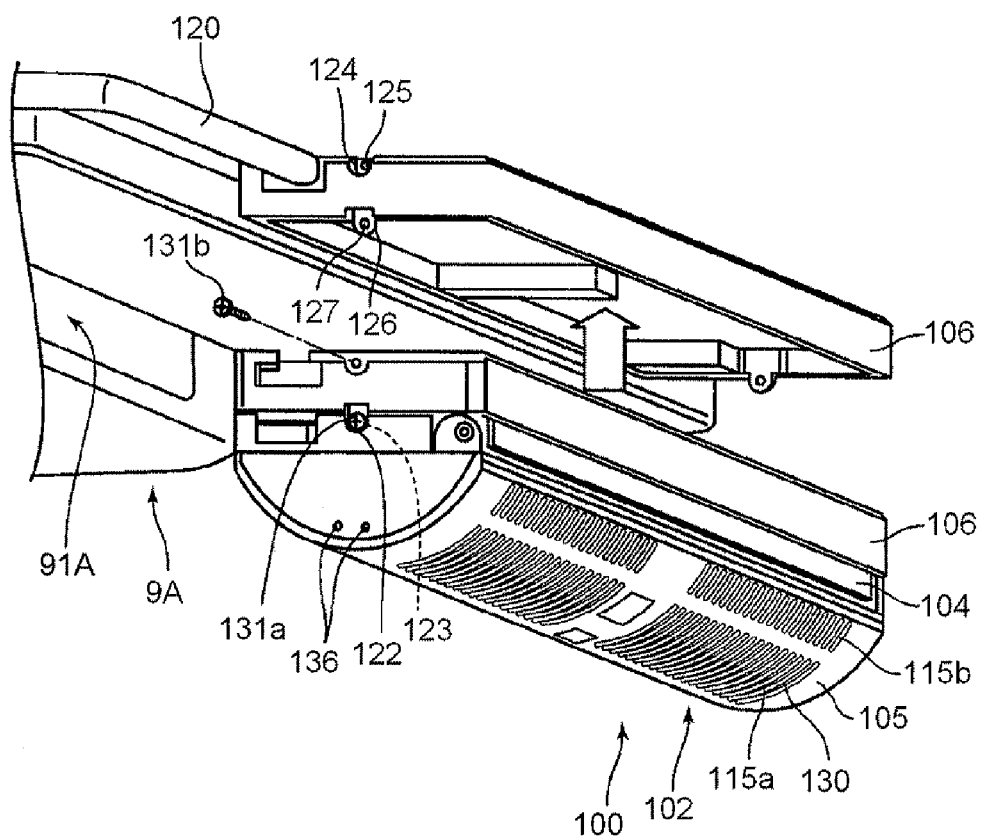
FIG. 19 is a perspective view illustrating placement of spacers for the air cleaner of FIG. 13 in progress.
Figure 20:
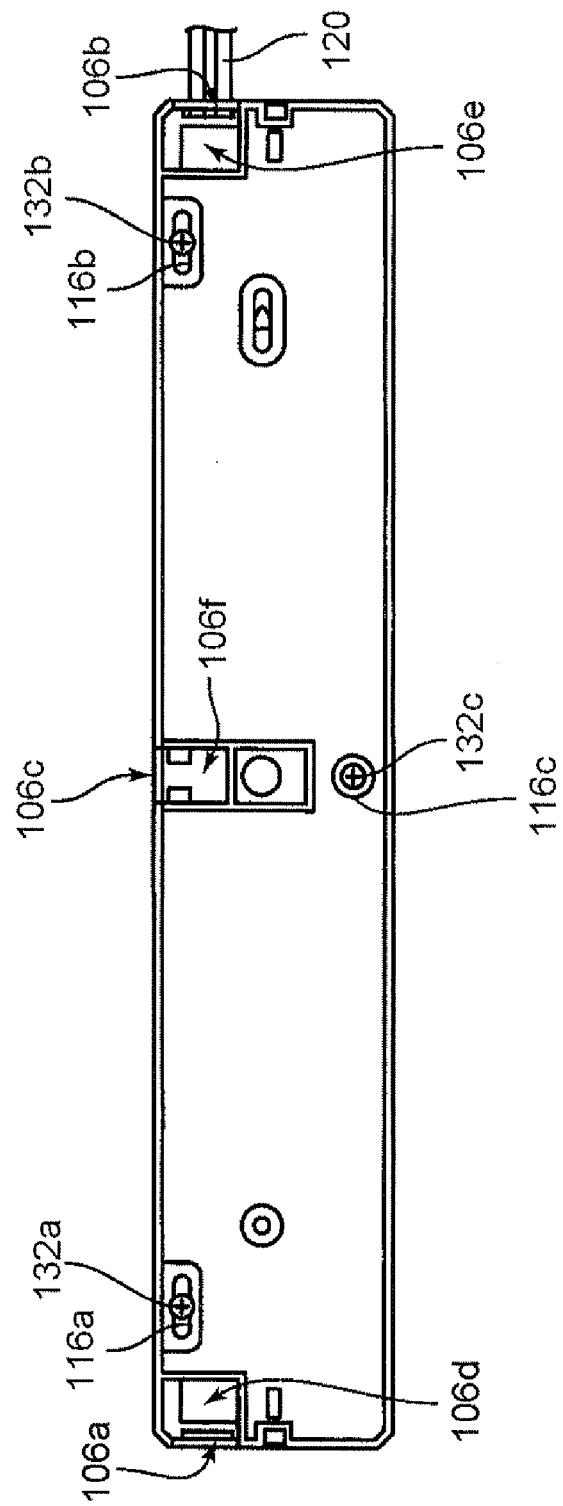
FIG. 20 is a plan view illustrating locations of screw holes of the spacer of FIG. 19.

As illustrated in FIGS. 14 to 16, the main body 102 basically includes: ion generation parts 103; a seating 104; and a cover 105. As illustrated in FIGS. 19 and 20, when necessary, the main body 102 further includes a spacer 106 for adjusting heights of introduction ports 114a and 114b of the cover 105 in accordance with height and/or direction of air discharged from the discharge port 91A. The spacer 106 is provided between the seating 104 and the ceiling surface CS.

Figure 21:
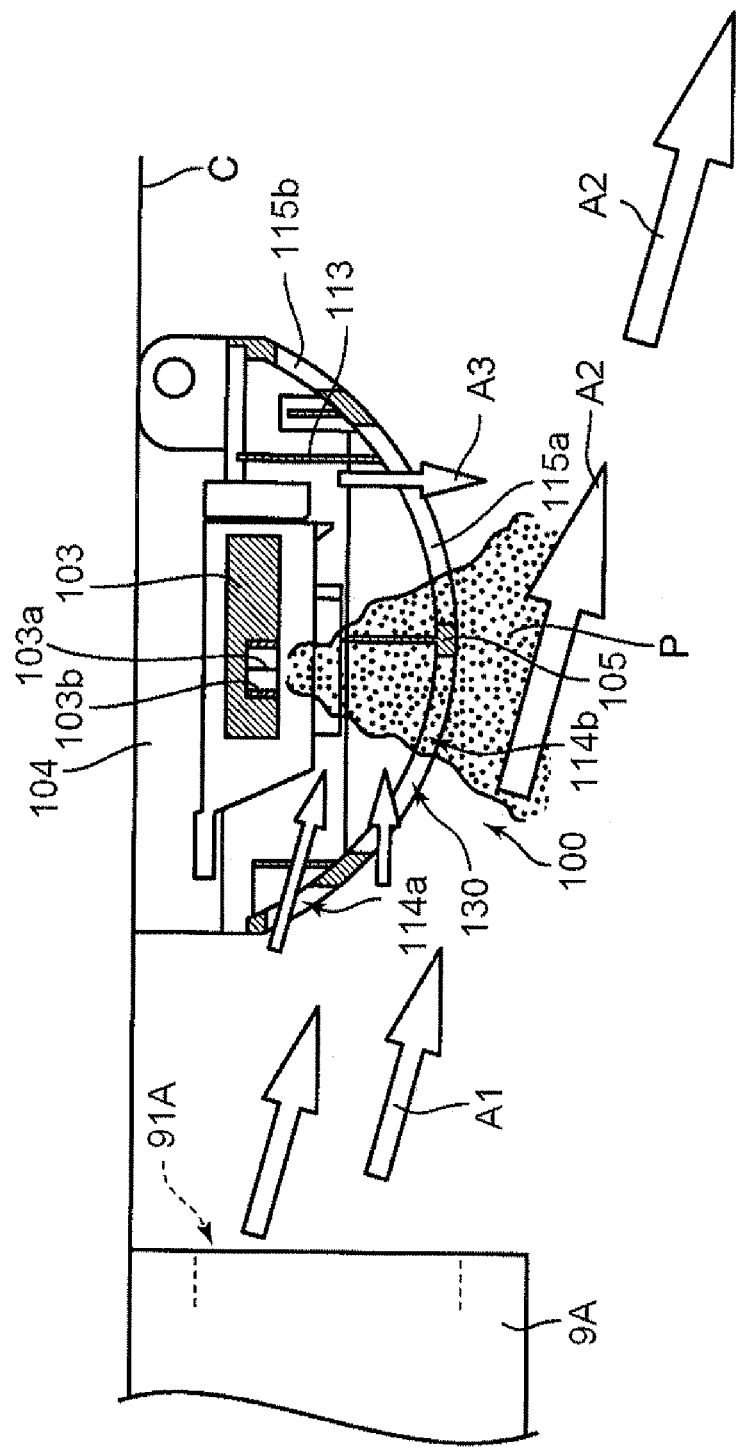
FIG. 21 is an explanatory cross-sectional view illustrating how air discharged from an air conditioner is cleaned by the air cleaner of FIG. 13.

As illustrated in FIG. 21, each ion generation part 103 has: needle-like discharge electrodes 103a; and annular induction electrodes 103b surrounding the needle-like discharge electrodes 103a. Each ion generation part 103 includes positive and negative needle-like discharge electrodes 103a. Voltages are applied to the needle-like discharge electrodes 103a, thereby generating the ions P for cleaning air discharged from the discharge port 91A. The ions P include positive ions, e.g., $H^+(H_2O)m$ (where m is any natural number), and negative ions, e.g., $O_2^-(H_2O)n$ (where n is any natural number), which are generated by applying voltages to the needle-like discharge electrodes 103a and ionizing water molecules in air, for example.

The seating 104 serves as a seating to which the ion generation parts 103 are fixed. The ion generation parts 103 are attached to an installation surface 104h of the seating 104 (i.e., a surface thereof located opposite to the ceiling surface CS), and fixed to the installation surface 104h of the seating 104 with the use of screws 134. In the example illustrated in FIG. 16, the two ion generation parts 103 are installed on the installation surface 104h of the single seating 104, but at least one ion generation part 103 may be installed thereon.

Further, as illustrated in FIG. 16, the seating 104 is provided with three openings 117a, 117b and 117c.

Furthermore, as illustrated in FIGS. 14 and 15 and FIG. 19, partially inwardly recessed attachment steps 122 are formed at lateral surfaces of the seating 104. Each attachment step 122 has a smooth arc-shaped inner peripheral surface. An internal screw hole 123 is formed in each of the attachment steps 122.

In addition, at three lateral surfaces of the seating 104, there are provided pull-out holes 104a, 104b and 104c through which the harness 120 for electrical connection with the other air cleaners 100 is pulled out. Sizes of the pull-out holes 104a, 104b and 104c are set so that the harness 120 and the molded cover covering the harness 120 can be inserted therethrough.

Moreover, in the seating 104, there are formed through holes 104e, 104f and 104g communicated with the pull-out holes 104a, 104b and 104c, respectively. The harness 120 is connected to the ion generation parts 103 through the through holes 104e, 104f and 104g.

Besides, as illustrated in FIG. 15, at the lateral surfaces of the seating 104, there is provided a circular cylindrical shaft 121 vertically protruded from the lateral surfaces.

Figure 18:
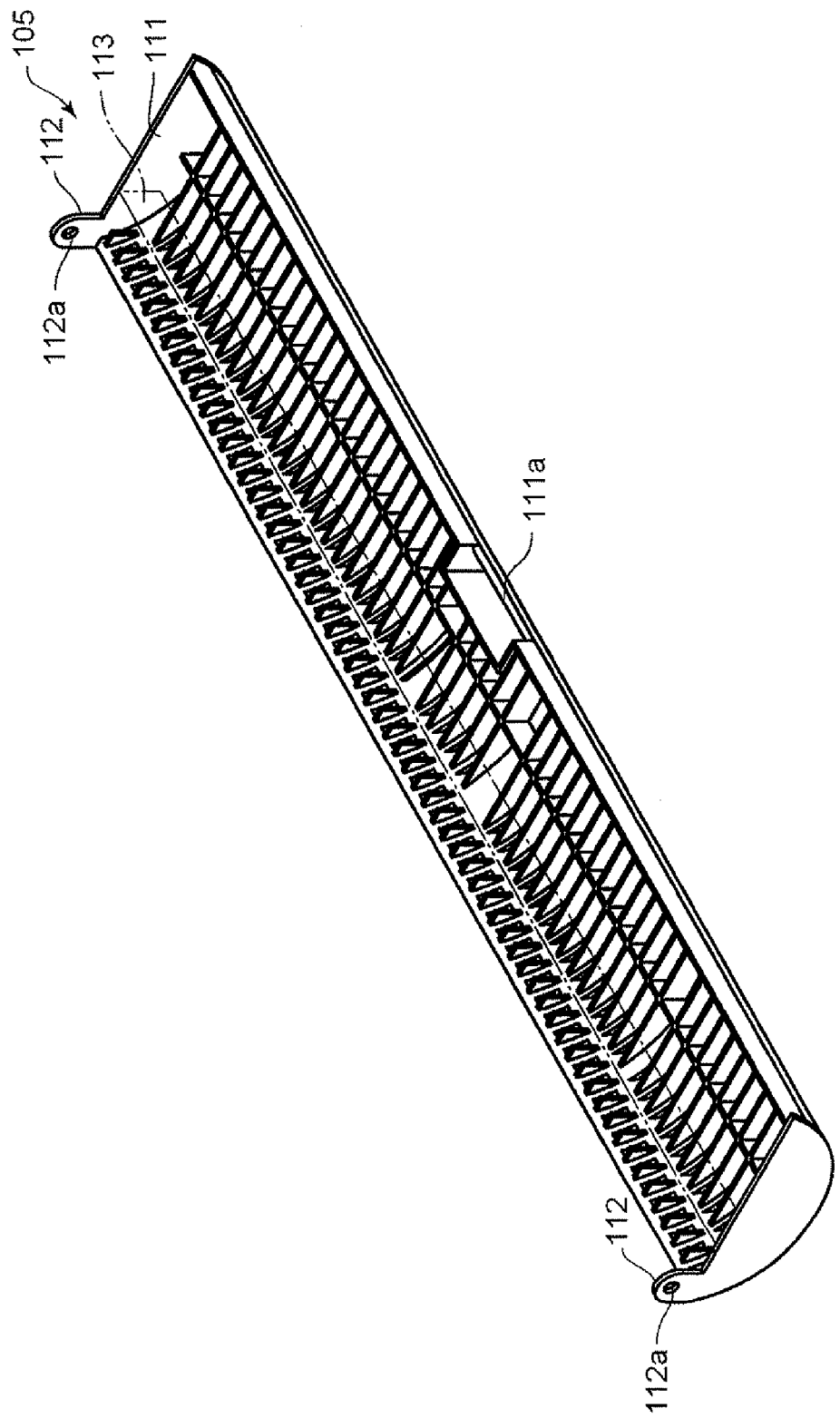
FIG. 18 is a perspective view illustrating inside of the cover of FIG. 16.

The cover 105 is a member for covering the ion generation parts 103, and is attached to the seating 104. As illustrated in FIGS. 14, FIG. 15, and FIG. 18, the cover 105 includes a cover main body 111 and hinge portions 112.

The cover main body 111 serves as an elongated cover having an arc-shaped surface, and is molded integrally with the hinge portions 112 and a guide portion 113 by using a synthetic resin.

At a semi-cylindrical peripheral surface of the cover main body 111, there are formed a plurality of slits 130 extending in a widthwise direction. The slits 130 include the introduction ports 114a and 114b and discharge ports 115a and 115b illustrated in FIG. 21.

As illustrated in FIG. 21, the introduction ports 114a and 114b are the slits through which air A1 discharged from the discharge port 91A of the air conditioner 9A is introduced. The discharge ports 115a and 115b are the slits through which the air, introduced into the inside of the cover 105 from the introduction ports 114a and 114b, and the ions P are discharged.

Accordingly, of the slits 130, the slits located closer to the discharge port 91A of the air conditioner 9A serve as the introduction ports 114a and 114b, and the slits located away from the discharge port 91A of the air conditioner 9A serve as the outlets 115a and 115b.

Further, as illustrated in FIGS. 15 and 16 and FIG. 18, an engagement portion 111a is formed at an edge of a center of the cover main body 111. The engagement portion 111a is engaged with a receiving portion 104d provided at a center of the seating 104, thereby locking the cover 105 in a closed state.

Furthermore, in the present embodiment, regions of the cover main body 111 facing the installation surface 104h of the seating 104, e.g., edges of the cover main body 111 extending on both sides of the engagement portion 111a, are provided with magnetic bodies such as steel plates (not illustrated). The magnetic bodies of the cover main body 111 are attracted to two magnets 135 provided at the installation surface 104h of the seating 104, thereby making it possible to reliably maintain the closed state of the cover 105. Moreover, when the engagement portion 111a and the receiving portion 104d are disengaged from each other and the cover 105 is opened against a magnetic force of the magnets 135 by a hand, the cover 105 can be easily opened and closed.

As illustrated in FIGS. 15 and 21, the hinge portions 112 protrude toward the seating 104 from the cover main body 111. The hinge portions 112 are rotatably connected to the shaft 121 protruded outward from the lateral surfaces of the seating 104 through holes 112a of the hinge portions 112.

Furthermore, as illustrated in FIG. 15, the hinge portions 112 and the shaft 121 are placed in regions of the main body 102 located away from the air conditioner 9A; therefore, the cover 105 can be opened by being rotated in a direction in which the cover 105 moves away from the air conditioner 9A so as not to collide with the air conditioner 9A.

As illustrated in FIG. 13 and FIGS. 19 and 20, when necessary, the spacer 106 is interposed between the seating 104 and the ceiling surface CS in order to adjust the heights of the introduction ports 114a and 114b of the cover 105 in accordance with the height and/or direction of air discharged from the discharge port 91A.

As illustrated in FIGS. 19 and 20, the spacer 106 is formed so as to be overlapped with the seating 104 and the other spacer 106, thus making it possible to adjust the heights of the introduction ports 114a and 114b by a given height (of about 20 mm) for each spacer 106.

Moreover, a shape of a surface of the spacer 106, placed on the ceiling surface CS, is similar to that of a surface of the seating 104 on which the spacer 106 is placed, and planar locations of screw holes 116a to 116c, for example, of the spacer 106 are similar to those of the openings 117a to 117c of the seating 104. Therefore, each anchor 83 located in the ceiling surface CS to fix the seating 104 can be used as it is, thus enabling fixation of the spacer 106. Specifically, the spacer 106 is fixed as follows.

As illustrated in FIG. 20, the spacer 106 is provided with the three screw holes 116a, 116b and 116c.

The screw holes 116a, 116b and 116c of the spacer 106 and the openings 117a, 117b and 117c of the seating 104 are formed so that the planar locations of the screw holes 116a, 116b and 116c and the planar locations of the openings 117a, 117b and 117c correspond to each other. Therefore, the screw holes 116a, 116b and 116c of the spacer 106 can be overlapped with the positions of the anchors 83 located in the ceiling surface CS to fix the seating 104. Accordingly, using the anchors 83 located at the corresponding positions in the ceiling surface CS, the seating 104 or the spacer 106 can be screwed thereto.

Further, at three lateral surfaces of the spacer 106, there are provided pull-out holes 106a, 106b and 106c through which the harness 120 for electrical connection with the other air cleaners 100 is pulled out. Sizes of the pull-out holes 106a, 106b and 106c are the same as those of the pull-out holes 104a, 104b and 104c of the seating 104, and are set so that the harness 120 and the molded cover covering the harness 120 can be inserted therethrough.

Furthermore, in the spacer 106, there are formed through holes 106d, 106e and 106f communicated with the pull-out holes 106a, 106b and 106c, respectively. The through holes 106d, 106e and 106f can be communicated with the through holes 104e, 104f and 104g of the seating 104, respectively, and through the through holes 106d, 106e, 106f, 104e, 104f and 104g, the harness 120 can be connected to the ion generation parts 103 placed on the surface of the seating 104.

As illustrated in FIG. 19, at the lateral surfaces of the spacer 106, attachment protrusions 126 are formed. The attachment protrusions 126 are provided with openings 127 through which lateral surface fixation screws 131a and 131b are inserted. Tips of the attachment protrusions 126 are arc-shaped.

Moreover, at the lateral surfaces of the spacer 106, partially inwardly recessed attachment steps 124 are formed. An internal screw hole 125 is formed in each of the attachment steps 124. Each attachment step 124 has a smooth arc-shaped inner peripheral surface.

As illustrated in FIGS. 18 and 21, the air cleaner 100 according to Embodiment 3 further includes the guide portion 113.

As illustrated in FIGS. 18 and 21, the guide portion 113 is provided inside the cover 105 and opposite to the introduction ports 114a and 114b with respect to the ion generation parts 103, and guides an air flow inside the cover 105 downward. The guide portion 113 is conceptually included in guide means of the present invention.

The attachment means for fixing the main body 102 to the ceiling surface CS includes screws, for example. Specifically, the attachment means includes: seating fixation screws 133a, 133b and 133c (see FIG. 16); the lateral surface fixation screws 131a and 131b (see FIG. 19); and spacer fixation screws 132a, 132b and 132c (see FIG. 20). These screws are conceptually included in the attachment means of the present invention.

In this embodiment, the seating fixation screws 133a, 133b and 133c (see FIG. 16) serve to fix the seating 104 to the ceiling C. The lateral surface fixation screws 131a (see FIG. 19) serve to fix the lateral surfaces of the spacer 106 and those of the seating 104 to each other. The lateral surface fixation screws 131b (see FIG. 19) serve to fix the lateral surfaces of the spacers 106 to each other. The spacer fixation screws 132a, 132b and 132c (see FIG. 20) serve to fix the spacer 106 to the ceiling C. Note that each lateral surface fixation screw 131a is conceptually included in a seating fixation member of the present invention.

The air cleaner 100 formed as described above is attached to the ceiling C as follows.

Figure 17:
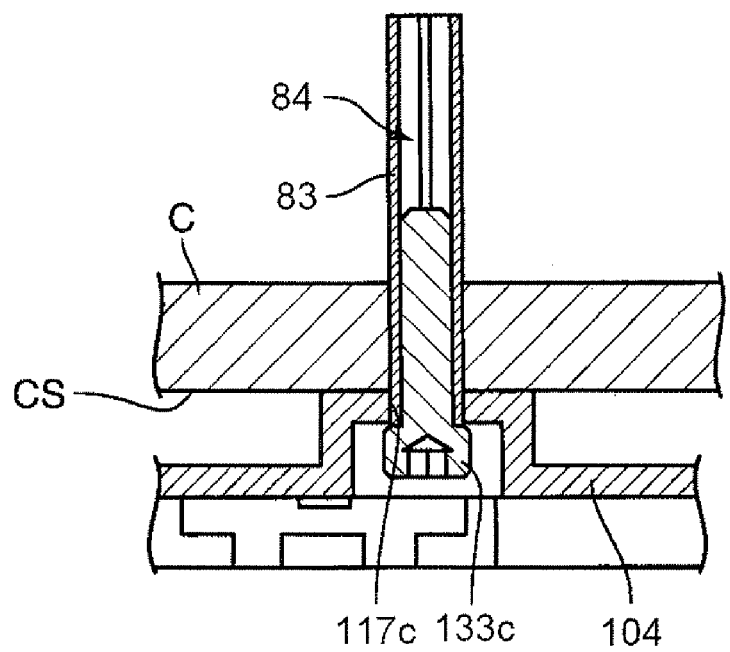
FIG. 17 is an enlarged cross-sectional view of a region in the vicinity of a screw for fixing a seating of FIG. 16 to a ceiling.

First, when the seating 104 is directly screwed to the ceiling C, the seating fixation screws 133a, 133b and 133c are inserted into the openings 117a, 117b and 117c of the seating 104, respectively, thus fixing the seating 104 to a region of the ceiling surface CS located downstream of the given discharge port 91A. Specifically, as illustrated in FIG. 17, the position of the anchor 83 embedded in a region of the ceiling C located downstream of the discharge port 91A and the position of the opening 117c are aligned; then, in this state, with the seating fixation screw 133c inserted into the opening 117c, the seating fixation screw 133c is screwed into an internal screw hole 84 of the anchor 83. As a result, the seating 104 is fixed along the ceiling surface CS.

When the spacer 106 is used, as illustrated in FIGS. 19 and 20, using the spacer fixation screws 132a, 132b and 132c, the lowermost spacer 106 is first screwed to positions corresponding to the anchors 83 (see FIG. 17) embedded in regions of the ceiling surface CS located downstream of the discharge port 91A of the air conditioner 9A. Then, the second spacer 106 or the seating 104 is superposed on and screwed to the lowermost spacer 106 with the use of the lateral surface fixation screws 131a or 131b.

When the second spacer 106 is attached, as illustrated in FIG. 19, the attachment protrusions 126 of the lowermost spacer 106 are inserted into the attachment steps 124 of the second spacer 106; then, in this state, the lateral surface fixation screws 131b are inserted into the openings 127 of the attachment protrusions 126 and screwed into the internal screw holes 125 of the attachment steps 124, thereby connecting the spacers 106 to each other. When the third spacer 106 is further attached, similar operations are performed.

Furthermore, when the seating 104 is attached to the second or subsequent spacer 106, similarly to the case where the spacers 106 are stacked, the attachment protrusions 126 of the spacer 106 are inserted into the attachment steps 122 of the seating 104; then, in this state, the lateral surface fixation screws 131a are inserted into the openings 127 of the attachment protrusions 126 and screwed into the internal screw holes 123 of the attachment steps 122, thereby connecting the seating 104 and the spacer 106 to each other.

Next, using the air cleaner 100 according to Embodiment 3, a method for cleaning the air Al discharged from the discharge port 91A of the air conditioner 9A will be described.

As illustrated in FIG. 21, first, when the air A1 discharged from the discharge port 91A of the air conditioner 9A is introduced into the inside of the cover 105 through the introduction ports 114a and 114b of the cover 105, part of the air is cleaned by the ions P generated by the ion generation parts 103. The air and the ions P are discharged outside of the cover 105 through the outlets 115a and 115b.

Further, as indicated by a downward flow A3 in FIG. 21, the part of the air, cleaned inside the cover 105, is guided downward by the guide portion 113 and discharged downward through the outlets 115a, and is then merged with air A2 flowing outside the cover 105, so that the resulting air is supplied to the interior of a room.

Moreover, the ions P generated by the ion generation parts 103 include positive and negative ions obtained by ionization and decomposition of water molecules in air, and the ions P each have a relatively long lifetime (e.g., a lifetime of about 3 seconds from its generation) since the ions P are covered with water molecules. Therefore, part of the ions P are discharged into a room together with the cleaned air, thus making it possible to further clean air in the room by the discharged ions P.

For example, as illustrated in FIG. 21, part of the ions P are discharged outside of the cover 105 through the slits 130 located below the needle-like discharge electrodes 103a; then, the discharged ions P clean the air A2 flowing outside the cover 105 and are supplied to a given area of the interior of a room together with the air A2, thus making it possible to clean air in the given area in a concentrated manner.

The main body 102 of the air cleaner 100 according to Embodiment 3 is placed downstream of the given discharge port 91A of the air conditioner 9A with the use of the attachment means such as the screws 131a, 131b, 132a to 132c, and 133a to 133c, thereby making it possible to clean air discharged from the given discharge port 91A and to supply the cleaned air to a given area of the interior of a room.

For example, in FIG. 13, the air cleaners 100 are placed downstream of all the discharge ports 91A for the four directions, but in the present invention, the air cleaner 100 may be placed downstream of any one of the discharge ports 91A for the four directions; for example, the air cleaner 100 may be placed downstream of only the discharge port 91A directed toward an area where many people are present. Thus, the cleaned air and the ions P can be supplied to the given area, so that the cleaned air can be effectively discharged.

Further, the main body 102 is placed outside of the air conditioner 9A. More specifically, the main body 102 is placed on a region of the ceiling surface CS located downstream of the discharge port 91A of the air conditioner 9A, and therefore, the air cleaner 100 can be more easily used in combination with an existing air conditioner as compared with a case where the main body 102 is placed inside the air conditioner 9A.

Furthermore, the main body 102 according to Embodiment 3 has: the seating 104 to which the ion generation parts 103 are fixed; and the cover 105 for covering the ion generation parts 103. In the cover 105, there are formed: the introduction ports 114a and 114b through which air discharged from the discharge port of the air conditioner 9A is introduced; and the outlets 115a and 115b through which the air and the ions P are discharged. In this structure, the cover 105 having the introduction ports 114a and 114b and the outlets 115a and 115b covers the ion generation parts 103, thereby making it possible to protect the ion generation parts 103. In addition, the air cleaned by the ions P and flow of the ions P can be discharged in the given direction from the outlets 115a and 115b.

The main body 102 according to Embodiment 3 further includes at least one spacer 106 interposed between the seating 104 and the ceiling surface CS. The attachment means includes: the lateral surface fixation screws 131a serving as the seating fixation members for fixing the seating 104 to the spacer 106; and the spacer fixation screws 132a, 132b and 132c for fixing the spacer 106 to the ceiling surface CS. In this structure, one or a plurality of the spacers 106 are interposed between the seating 104 and the ceiling surface CS, thus making it possible to perform positioning of the introduction ports 114a and 114b of the cover 105 in accordance with the position and/or wind direction of the discharge port 91A.

Moreover, the spacer 106 has the screw holes 116a, 116b and 116c through which the spacer fixation screws 132a, 132b and 132c for fixing the spacer 106 to the ceiling surface CS are inserted; in addition, in the seating 104, the openings 117a, 117b and 117c are formed so that the planar locations thereof correspond to those of the screw holes 116a, 116b and 116c of the spacer 106. In this structure, the planar locations of the screw holes for screwing of the seating 104 to the ceiling surface CS and those of the screw holes for screwing of the spacer 106 to the ceiling surface CS correspond to each other; hence, using the anchors 83 located at the corresponding positions in the ceiling surface CS, the seating 104 or the spacer 106 can be screwed thereto.

For example, when the air cleaner 100 is initially placed on the ceiling surface CS, the seating 104 is directly screwed to the ceiling surface CS without the use of the spacer 106. However, when the heights of the introduction ports 114a and 114b of the cover 105 need to be adjusted afterwards because, for example, the direction of air discharged from the air conditioner 9A is changed, each anchor 83 used for fixation of the seating 104 to the ceiling surface CS is used as it is, thus allowing the additional spacer 106 to be screwed to the ceiling surface CS.

In addition, the air cleaner 100 according to Embodiment 3 further includes the guide portion 113 that is provided inside the cover 105 and opposite to the introduction ports 114a and 114b with respect to the ion generation parts 103, and that guides the air flow inside the cover 105 downward; thus, as indicated by the downward flow A3 in FIG. 21, the air, cleaned inside the cover 105, can be smoothly guided downward by the guide portion 113. As a result, the amount of the cleaned air and the ions P supplied to the given area can be increased.

Besides, in Embodiment 3, the cover 105 has: the cover main body 111; and the hinge portions 112 protruded toward the seating 104 from the cover main body 111, and the hinge portions 112 are rotatably connected to the seating 104. Since the cover 105 is connected to the seating 104 only through the hinge portions 112 protruded from the cover main body 111 in this manner, the cover 105 can be easily detached.

Further, the hinge portions 112 and the shaft 121 according to Embodiment 3 are placed in regions of the main body 102 located away from the air conditioner 9A, and the cover 105 can be opened by being rotated in a direction in which the cover 105 moves away from the air conditioner 9A; therefore, it is possible to easily open and close the cover 105 while preventing the cover 105 from colliding with the air conditioner 9A. Furthermore, when a stepladder is placed directly below the air conditioner 9A, the cover 105 is moved away from the air conditioner 9A upon opening of the cover 105, thus making it possible to easily perform, for example, maintenance of the inside of the air cleaner 100 without being encumbered by the cover 105.

Moreover, in Embodiment 3, the pull-out holes 104a, 104b and 104c, through which the harness 120 including electric wires for electric connection with the ion generation parts 103 is pulled out, are formed at an externally exposed outer peripheral surface of the seating 104, thus allowing the harness 120 to be pulled out through the outer peripheral surface of the seating 104. Hence, routing of the harness 120 along the ceiling surface CS is considerably facilitated.

Further, in Embodiment 3, the pull-out holes 106a, 106b and 106c are also formed at an outer peripheral surface of each spacer 106, thus considerably facilitating the routing of the harness 120 along the ceiling surface CS even when the spacers 106 are used by being overlapped with the seating 104.

In addition, the planar locations of the pull-out holes 104a, 104b and 104c of the seating 104 and those of the pull-out holes 106a, 106b and 106c of each spacer 106 correspond to each other; thus, even when the additional spacer 106 is provided, it is possible to use the harness 120, routed along the ceiling surface CS at the time of initial placement of the air cleaner 100, as it is without changing the position of the harness.

In Embodiment 3, the example in which the guide portion 113 is formed integrally with the cover main body 111 and the hinge portions 112 has been described, but the present invention is not limited to this example; alternatively, the guide portion 113 may be fabricated separately from the cover main body 111, and may be detachably attachable to the cover main body 111.

<Embodiment 4>

In Embodiment 3 described above, the guide portion 113 for guiding the flow of air inside the cover 105 downward is formed so as to be protruded from an inner peripheral surface of the cover main body 111, but the present invention is not limited to this structure; alternatively, a wall of the inner peripheral surface of the cover main body 111 itself may be used as a guide portion.

Figure 22:
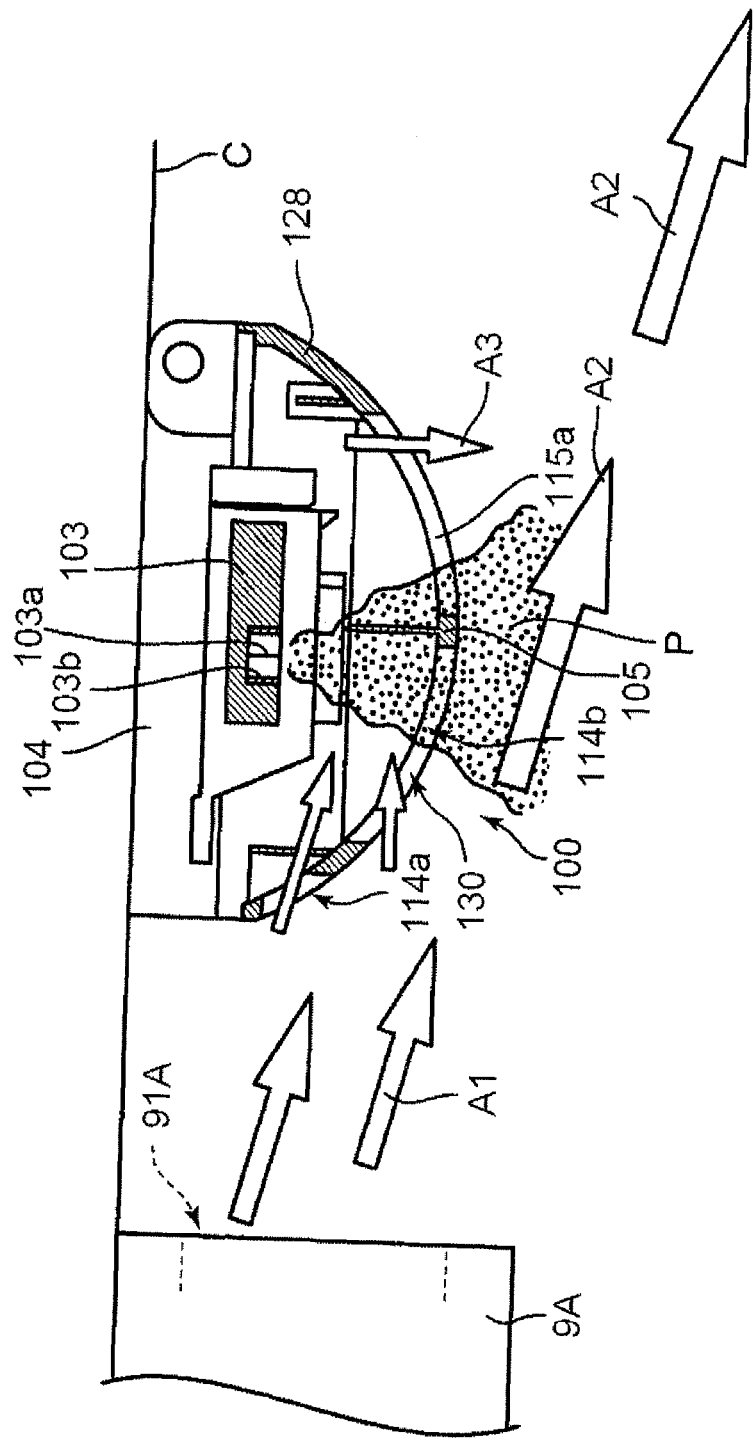
FIG. 22 is a cross-sectional view of an air cleaner according to Embodiment 4 of the present invention, in which a guide portion is formed by an inner peripheral surface of a cover.

Specifically, as illustrated in FIG. 22, of the slits 130 formed in part of the inner peripheral surface of the cover main body 111 of the cover 105, part of the slits corresponding to the most downstream outlets 115b (see FIG. 21) are filled, and thus a guide portion 128 is molded integrally with the cover main body 111 of the cover 105.

In Embodiment 4, the inner peripheral surface of the cover main body 111 is used as the guide portion 128, thereby allowing the air cleaned inside the cover 105 and the ions P to be smoothly guided downward as indicated by the downward flow A3 in FIG. 22. In addition, since the guide portion 128 is formed by the inner peripheral surface of the cover main body 111, the cover 105 and the guide portion 128 can be extremely easily molded.

Note that in Embodiments 3 and 4 described above, screws have been described as the attachment means for fixing the main body to the ceiling surface by way of example, but the present invention is not limited to this example; alternatively, any means may be used as long as it can fix the main body to the ceiling surface. Other than screws, various attachment means such as bolts, nuts or nails, for example, may be used.

Furthermore, in Embodiments 3 and 4, the cover 105 is connected to the seating 104 via the hinge portions 112, but in order to prevent the cover 105 from falling down, the cover 105 and the seating 104 are preferably further connected to each other with a wire, for example.

Moreover an "air wing", for example, may be attached to an outer portion of the cover 105 in order to adjust the direction of air flow discharged from the discharge port 91A of the air conditioner 9A. For example, as illustrated in FIG. 19, attachment holes 136 for attachment of an "air wing" are preferably formed at longitudinal lateral surfaces of the cover 105.

Figure 23:
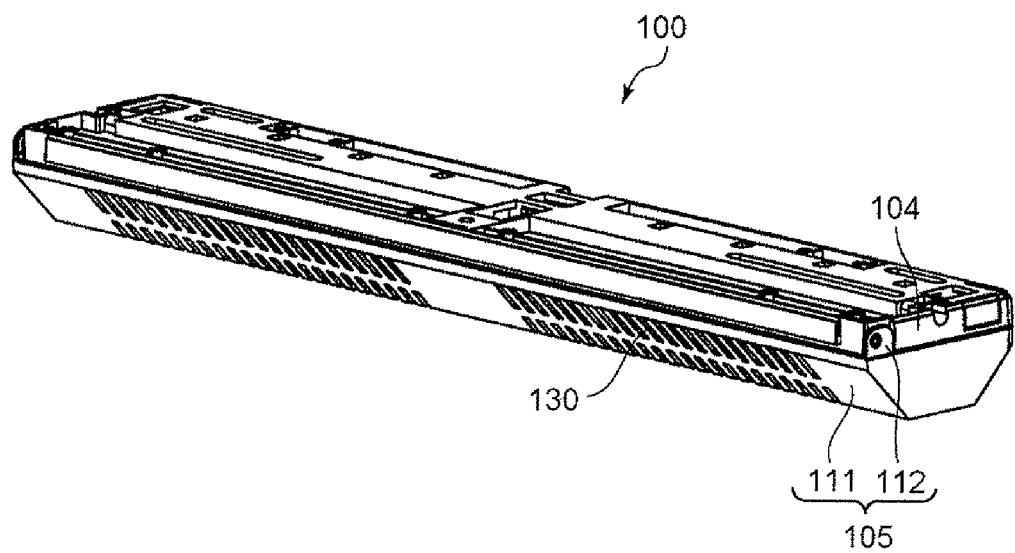
FIG. 23 is a perspective view illustrating a variation of the air cleaner according to the present invention, in which a cover main body has a trapezoidal shape.
Figure 24:
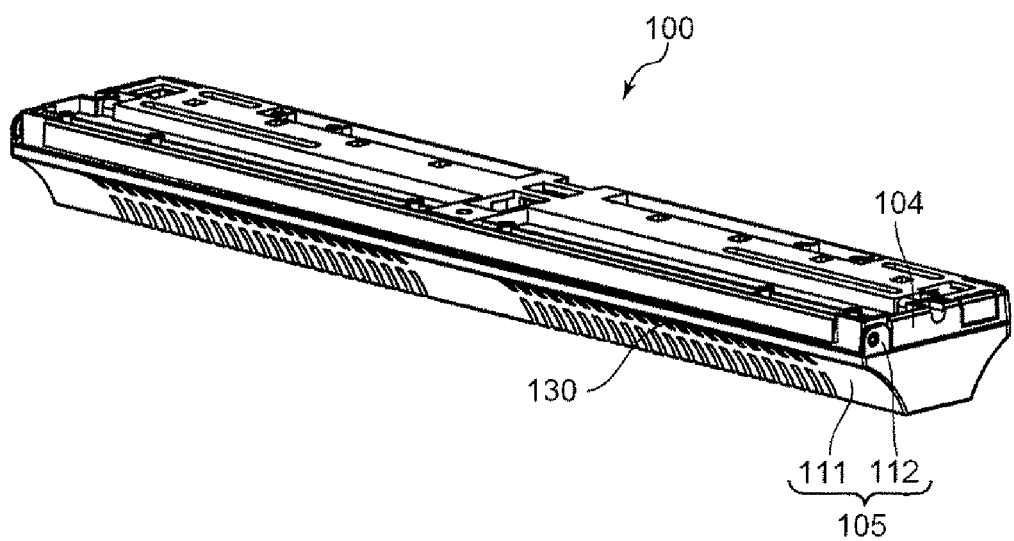
FIG. 24 is a perspective view illustrating another variation of the air cleaner according to the present invention, in which oblique surfaces of the trapezoidal shape of the cover main body are curved inwardly.

Note that in Embodiments 3 and 4 described above, the example in which the cover main body 111 is formed into a semi-circular cylindrical shape having an arc-shaped surface has been described, but the present invention is not limited to this example; alternatively, the cover main body having any of various shapes may be used. For example, the cover main body 111 having a trapezoidal shape as illustrated in FIG. 23 or having a trapezoidal shape in which oblique surfaces thereof are curved inwardly as illustrated in FIG. 24 may be used. Also in such a case, effects similar to those of Embodiments 3 and 4 are achievable.

Furthermore, shapes of the slits 130 formed in the cover main body 111 may be varied; for example, widths of the slits 130 may be increased.

REFERENCE SIGNS LIST 1 ion generator
2 ion generation device 21 ion generation part
22 ion generation part
3 casing
31*a* attachment surface
34 wind guide surface
4 inlet
51 first outlet
52 second outlet
6 wind barrier plate (plate piece, guide portion)
7 air passage
8 ceiling (attachment target)
S slit opening
9A air conditioner (air conditioning apparatus)
91A discharge port
100 air cleaner
102 main body
103 ion generation part
104 seating
104*a*, 104*b*, 104*c* pull-out hole
105 cover
106 spacer
111 cover main body
112 hinge portion
113 guide portion (guide means)
114*a*, 114*b* introduction port
115*a*, 115*b* outlet
116*a*, 116*b*, 116*c* screw hole
117*a*, 117*b*, 117*c* opening
120 harness (electric wires)
128 guide portion (guide means)
130 slit
131*a* lateral surface fixation screw (seating fixation member, attachment means)
131*b* lateral surface fixation screw (attachment means)
132*a*, 132*b*, 132*c* spacer fixation screw (spacer fixation member, attachment means)
133*a*, 133*b*, 133*c* seating fixation screw (attachment means)
C ceiling
CS ceiling surface

The invention claimed is:

1. An ion generator comprising:
a casing that has an inlet through which air can flow in from outside and an outlet through which air can flow out to outside;
an air passage through which the inlet and the outlet are connected to each other in the casing;
and an ion generation device for discharging ions into the air passage,
wherein the casing has, at its outer surface, an inclined wind guide surface, and the inlet is provided at the wind guide surface,
wherein the casing has another outer surface that forms an acute interior angle with the wind guide surface and serves as an attachment surface for an attachment target,
wherein the inlet is provided in a region of the wind guide surface, the distance of which from the attachment surface is shorter,
wherein a first outlet is provided in a region of the wind guide surface, the distance of which from the attachment surface is longer,
wherein a second outlet is provided in a region of the casing at which an end of the wind guide surface provided with the first outlet is connected to the attachment surface,
wherein the air passage is internally provided with a guide portion by which part of air flowing from the inlet toward the second outlet is guided to the first outlet, and
wherein the ion generation device is provided closer to the inlet than the guide portion.

2. The ion generator according to claim 1,
wherein each of the inlet and the first outlet is a slit opening extended in parallel with a direction in which the region of the wind guide surface, the distance of which from the attachment surface is shorter, and the region of the wind guide surface, the distance of which from the attachment surface is longer, are connected to each other, and a plurality of the slit openings are arranged in a direction intersecting the direction in which the region of the wind guide surface, the distance of which from the attachment surface is shorter, and the region of the wind guide surface, the distance of which from the attachment surface is longer, are connected to each other, and
wherein the inlet and the first outlet are located in the same position in the arrangement direction.

3. The ion generator according to claim 2,
wherein a width of each of a plurality of the slit openings in the arrangement direction thereof is wider than a distance between ends of the slit openings adjacent to each other in the arrangement direction thereof.

4. The ion generator according to claim 1,
wherein the inlet and the first outlet are continuous with each other in a direction in which the region of the wind guide surface, the distance of which from the attachment surface is shorter, and the region of the wind guide surface, the distance of which from the attachment surface is longer, are connected to each other, so that the inlet and the first outlet constitute a slit opening extended in parallel with the direction, and a plurality of the slit openings are arranged in a direction intersecting the direction in which the region of the wind guide surface, the distance of which from the attachment surface is shorter, and the region of the wind guide surface, the distance of which from the attachment surface is longer, are connected to each other.

5. The ion generator according to claim 1,
wherein the guide portion is a plate piece protruded from an inner surface of the casing toward an inner region of the air passage.

6. The ion generator according to claim 1,
wherein the ion generation device has an ion generation part for discharging ions toward opposite to the attachment surface.

7. The ion generator according to claim 1,
wherein the casing comprises a base and a cover for covering the base from below,
wherein, the cover forms an approximately inverted triangle shape in side view and the cover includes two inclined surface parts,
wherein one of the two inclined surface parts comprises the wind guide surface.

8. An air cleaner to clean air discharged from a discharge port of an air conditioner placed on a ceiling, wherein the air cleaner comprises:
a main body having an ion generation part for discharging ions to clean air discharged from the discharge port; and
attachment parts for fixing the main body to a region of a ceiling surface located downstream of the discharge port,
wherein the main body has: a seating to which the ion generation part is fixed; and a cover for covering the ion generation part, and
wherein the cover is provided with: an introduction port through which air discharged from the discharge port of the air conditioner is introduced; and an outlet through which the ions are discharged together with the air introduced to inside of the cover from the introduction port, wherein the main body comprises at least one spacer interposed between the seating and the ceiling surface, and wherein the attachment part comprises:

a fixation member for fixing the seating to the spacer; and a spacer fixation member for fixing the spacer to the ceiling surface.

9. The air cleaner according to claim 8, wherein the spacer fixation member is a screw, wherein the spacer has a screw hole through which the screw for fixing the spacer to the ceiling surface is inserted, and wherein the seating is provided with an opening so that a planar location of the opening and that of the screw hole of the spacer correspond to each other.

10. The air cleaner according to claim 8, wherein the air cleaner further comprises a guide part provided inside the cover and opposite to the introduction port with respect to the ion generation part, the guide part guiding an air flow inside the cover downward.

11. The air cleaner according to claim 10, wherein the guide part is molded integrally with the cover by filling part of the outlet of the cover.

12. The air cleaner according to claim 8, wherein the cover is openable by being rotated in a direction in which the cover moves away from the air conditioner.

13. The air cleaner according to claim 8, wherein the cover has:

a cover main body; and a hinge portion protruded from the cover main body toward the seating, and wherein the hinge portion is rotatably connected to the seating.

14. The air cleaner according to claim 8, wherein at an externally exposed outer peripheral surface of the seating, there is formed a pull-out hole through which an electric wire for connection with the ion generation part is pulled out.

15. An air cleaner to clean air discharged from a discharge port of an air conditioner placed on a ceiling, wherein the air cleaner comprises:

a main body having an ion generation part for discharging ions to clean air discharged from the discharge port; and attachment parts for fixing the main body to a region of a ceiling surface located downstream of the discharge port, wherein the main body has: a seating to which the ion generation part is fixed; and a cover for covering the ion generation part, and wherein the cover is provided with:

an introduction port through which air discharged from the discharge port of the air conditioner is introduced; and an outlet through which the ions are discharged together with the air introduced to inside of the cover from the introduction port, and wherein the air cleaner further comprises a guide part provided inside the cover and opposite to the introduction port with respect to the ion generation part, the guide part guiding an air flow inside the cover downward.

16. The air cleaner according to claim 15, wherein the guide part is molded integrally with the cover by filling part of the outlet of the cover.

17. The air cleaner according to claim 15, wherein the cover is openable by being rotated in a direction in which the cover moves away from the air conditioner.

18. The air cleaner according to claim 15, wherein the cover has: a cover main body; and a hinge portion protruded from the cover main body toward the seating, and wherein the hinge portion is rotatably connected to the seating.

19. The air cleaner according to claim 15, wherein at an externally exposed outer peripheral surface of the seating, there is formed a pull-out hole through which an electric wire for connection with the ion generation part is pulled out.

* * * * *